(12) United States Patent
Solotoff

(10) Patent No.: US 12,403,029 B1
(45) Date of Patent: Sep. 2, 2025

(54) DUAL-HANDED WRIST BRACE WITH ENHANCED THUMB SUPPORT

(71) Applicant: PREFERRED PRESCRIPTION, INC., Hollywood, FL (US)

(72) Inventor: Brandon Solotoff, Boca Raton, FL (US)

(73) Assignee: PREFERRED PRESCRIPTION, INC., Hollywood, FL (US)

( * ) Notice: Subject to any disclaimer, the term of this patent is extended or adjusted under 35 U.S.C. 154(b) by 557 days.

(21) Appl. No.: 17/192,359

(22) Filed: Mar. 4, 2021

Related U.S. Application Data

(60) Provisional application No. 62/984,839, filed on Mar. 4, 2020.

(51) Int. Cl.
 *A61F 5/01* (2006.01)
(52) U.S. Cl.
 CPC ................... *A61F 5/0118* (2013.01)
(58) Field of Classification Search
 CPC ........ A61F 5/0118; A61F 5/0104; A61F 5/01; A61F 5/05866; A61F 5/05858; A61F 5/05841; A61F 2007/0035; A61F 13/107; A61F 13/108; A61F 5/0102; A61F 5/00; A61F 5/013; A61F 5/05875; A61F 2007/0036; A61F 2007/0037; A61F 2007/0038; A61F 2007/0029;
(Continued)

(56) References Cited

U.S. PATENT DOCUMENTS 3,347,547 A 10/1967 Hynes
3,369,258 A 2/1968 Smith
(Continued)

FOREIGN PATENT DOCUMENTS

CA 735700 6/1966
CN 204072431 U 1/2015
(Continued)

OTHER PUBLICATIONS

Press Fit Forces Stress Design Calculator, Jun. 18, 2018, available at: www.engineersedge.com/calculators/machine-design/press-fit/press-fit.htm.
(Continued)

*Primary Examiner* — Victoria Hicks Fisher
(74) *Attorney, Agent, or Firm* — Thomas A. O'Rourke; James Rongiorno; O'ROURKE IP LAW PLLC

(57) ABSTRACT

A wrist brace, accommodating right and left hands, includes: a casing, pull tab, elastic members, center stay, and thumb stay. The casing includes: first and second thumb sockets, respectively usable for right and left thumbs, positioned symmetrically about the casing's center axis; and first and second elongated pockets, each formed parallel to the center axis, extending between the respective thumb socket and distal end of the casing. A third elongated pocket, centered on the center axis, extends between proximal and distal ends of the casing. The elastic securing members pass through holes on one side of the casing, with respective first ends fixedly secured to the pull tab, and respective second ends fixedly secured to another side of the casing. A center stay occupies the third pocket. A thumb stay is received within either of the first and second elongated pockets for respective use on the right and left hands.

10 Claims, 35 Drawing Sheets

(58) Field of Classification Search
CPC .............. A61F 13/104; A61F 13/105; A61F 2005/0186; A61F 13/10
USPC .......................................................... 602/21
See application file for complete search history.

(56) References Cited

U.S. PATENT DOCUMENTS

| | | | |
|---|---|---|---|
| 3,547,112 A | 12/1970 | Courtney | |
| 3,779,550 A | 12/1973 | Benoun | |
| 4,089,070 A | 5/1978 | Cherry | |
| 4,138,108 A | 2/1979 | Robinson | |
| 4,441,490 A | 4/1984 | Nirschi | |
| 4,619,250 A | 10/1986 | Hasegawa | |
| 4,671,258 A | 6/1987 | Barthlome | |
| 4,675,914 A | 6/1987 | Mitchell | |
| 4,716,892 A | 1/1988 | Brunswick | |
| 4,854,309 A | 8/1989 | Elsey | |
| 4,883,073 A | 11/1989 | Aziz | |
| 4,907,574 A | 3/1990 | Hollerbach | |
| 4,953,568 A | 9/1990 | Theisler | |
| 5,020,515 A | 6/1991 | Mann | |
| 5,056,504 A | 10/1991 | Mann | |
| 5,152,740 A | 10/1992 | Harkensee | |
| D339,866 S | 9/1993 | Rice | |
| 5,267,943 A | 12/1993 | Dancyger | |
| D347,693 S | 6/1994 | Dancyger | |
| 5,335,916 A | 8/1994 | Nee | |
| 5,383,827 A | 1/1995 | Stern | |
| D357,745 S | 4/1995 | Radwell | |
| 5,415,624 A | 5/1995 | Williams | |
| 5,437,620 A | 8/1995 | Shelly | |
| 5,513,657 A | 5/1996 | Nelson | |
| 5,566,389 A | 10/1996 | Li | |
| 5,600,849 A | 2/1997 | Hu | |
| 5,722,092 A | 3/1998 | Borzecki | |
| 5,728,059 A * | 3/1998 | Wiesemann | A61F 5/0118 128/878 |
| 5,759,166 A * | 6/1998 | Nelson | A61F 5/0118 602/21 |
| 5,813,050 A | 9/1998 | Popowski | |
| 5,819,313 A | 10/1998 | McCrane | |
| D403,425 S | 12/1998 | Taylor | |
| D405,180 S | 2/1999 | Reina | |
| 5,865,783 A | 2/1999 | Klimoski | |
| 5,873,130 A | 2/1999 | Lafferty | |
| 5,928,172 A | 7/1999 | Gaylord | |
| 6,024,715 A | 2/2000 | Maxwell | |
| 6,186,969 B1 | 2/2001 | Bell | |
| 6,196,985 B1 | 3/2001 | Slautterback | |
| 6,261,252 B1 | 7/2001 | Darcey | |
| 6,422,975 B1 | 7/2002 | Chermak | |
| D461,901 S | 8/2002 | Rodgers | |
| 6,454,681 B1 | 9/2002 | Brassil | |
| D465,068 S | 10/2002 | Payne | |
| 6,517,501 B1 | 2/2003 | Slautterback | |
| 6,547,752 B2 | 4/2003 | Holland | |
| 6,561,994 B1 | 5/2003 | Mills | |
| 6,673,028 B1 | 1/2004 | Argenta | |
| 6,893,410 B1 | 5/2005 | Hely | |
| 6,960,176 B1 | 11/2005 | Hely | |
| 7,033,331 B1 | 4/2006 | Hely | |
| 7,037,285 B2 | 5/2006 | Yewer | |
| 7,056,298 B1 | 6/2006 | Weber | |
| D533,280 S | 12/2006 | Wyatt | |
| 7,402,148 B2 | 7/2008 | Brewer | |
| 7,402,149 B1 | 7/2008 | Garelick | |
| 7,537,577 B2 | 5/2009 | Phelan | |
| 7,713,223 B2 | 5/2010 | Weber | |
| 7,824,352 B2 | 11/2010 | Jaccard | |
| 7,874,997 B2 | 1/2011 | Jaccard | |
| 7,914,475 B2 | 3/2011 | Wyatt | |
| 8,147,438 B2 | 4/2012 | Livolsi | |
| 8,235,927 B2 * | 8/2012 | Bauerfeind | A61F 5/0118 602/20 |
| 9,504,282 B1 * | 11/2016 | Frederick | A41D 19/01582 |
| 9,872,792 B2 | 1/2018 | Romo | |
| 10,842,661 B1 * | 11/2020 | Gaylord | A61F 5/05875 |
| 2004/0049141 A1 | 3/2004 | Slautterback | |
| 2005/0197609 A1 | 9/2005 | Mills | |
| 2006/0287626 A1 | 12/2006 | Bennett | |
| 2007/0225630 A1 | 9/2007 | Wyatt | |
| 2009/0012438 A1 | 1/2009 | Frangi | |
| 2011/0130694 A1 * | 6/2011 | Livolsi | A61F 5/0118 602/21 |
| 2013/0211304 A1 * | 8/2013 | Romo | A61F 5/013 602/21 |

FOREIGN PATENT DOCUMENTS

| | | |
|---|---|---|
| DE | 102015000783 A1 | 7/2016 |
| FR | 2576512 A1 | 8/1986 |
| WO | WO 2007/051524 | 5/2007 |

OTHER PUBLICATIONS

"Three General Types of Fit," available at www.mmto.org/dclark/Reports/Encoder%20Upgrade/fittolerences%20%5BRead-Only%5D.pdf., Jul. 8, 2019.

"Engineering Fit," available at: https://en.wikipedia.org/wiki/Engineering_fit, Jul. 8, 2019.

* cited by examiner

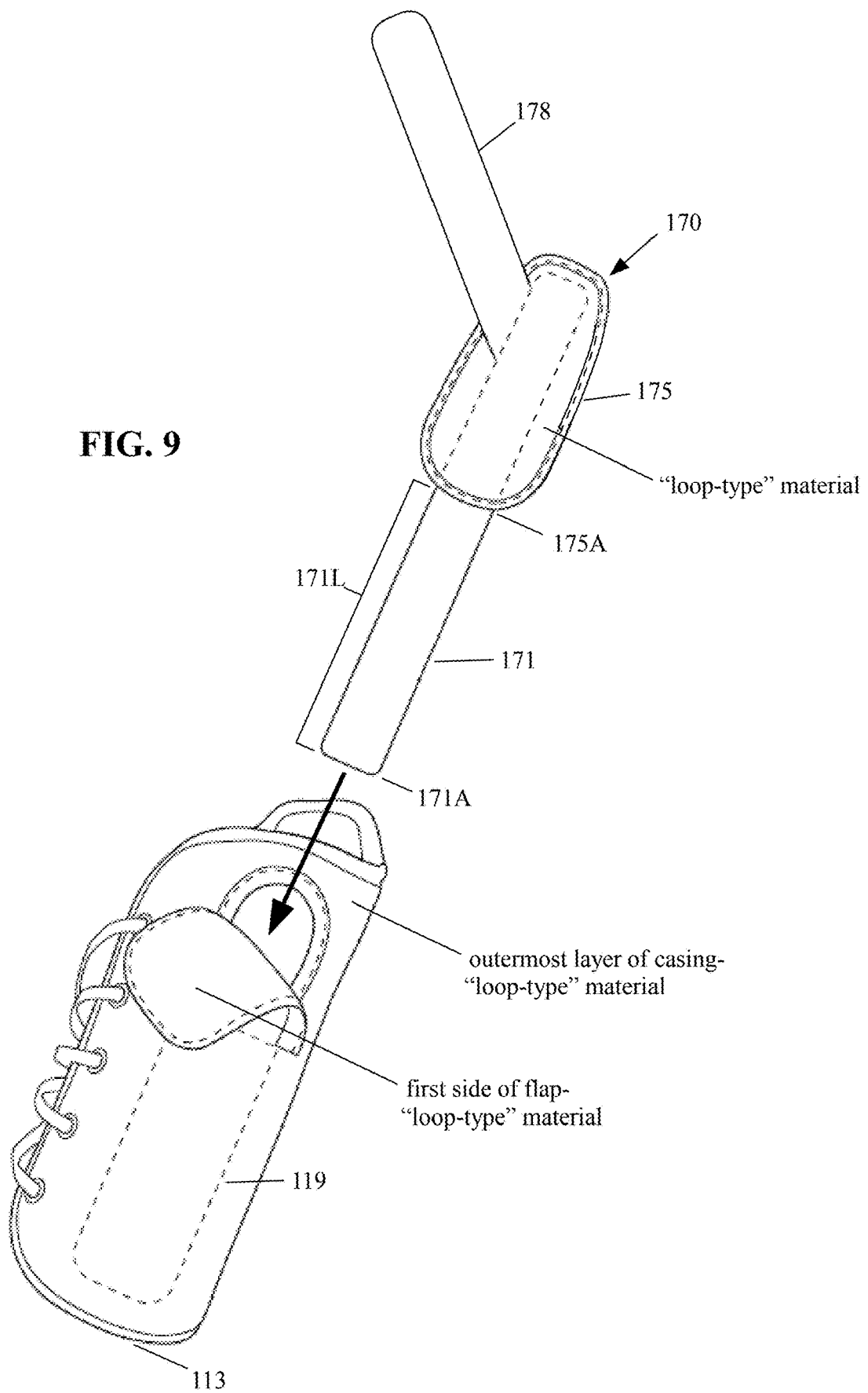

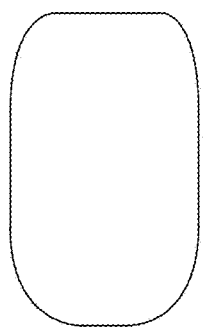
FIG. 30
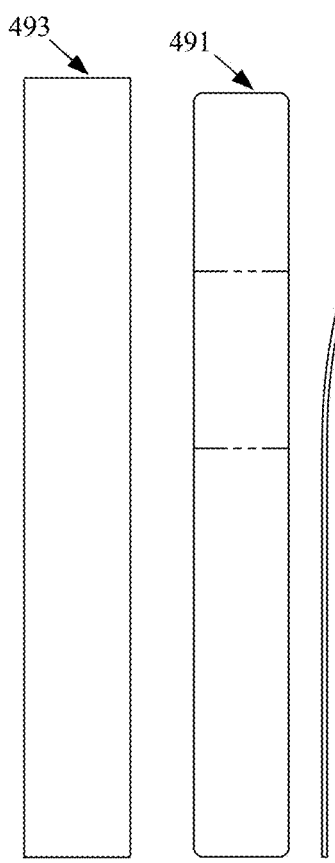
FIG. 31  FIG. 33
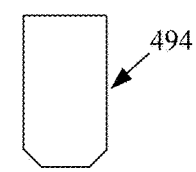
FIG. 32
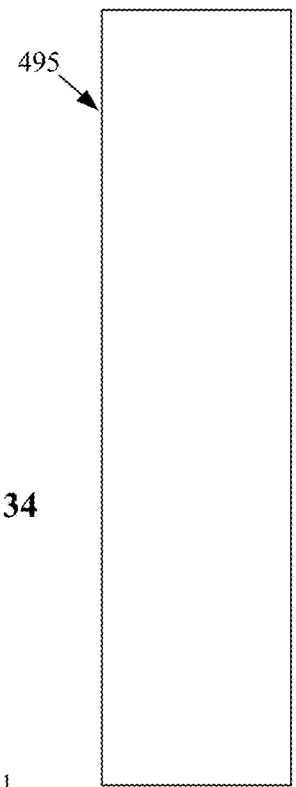
FIG. 35
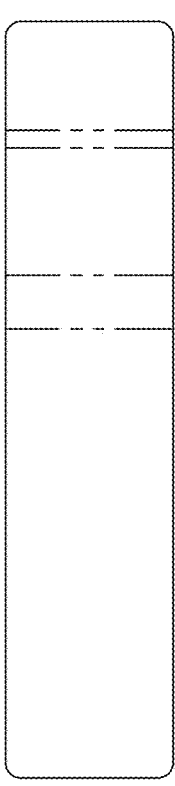
FIG. 37
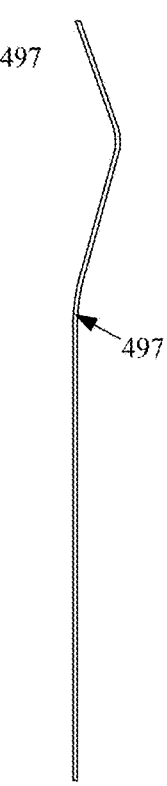
FIG. 38
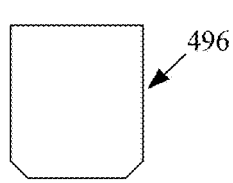
FIG. 36
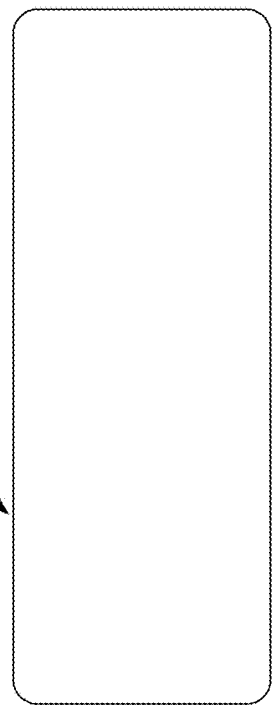
FIG. 39

DUAL-HANDED WRIST BRACE WITH ENHANCED THUMB SUPPORT

CROSS REFERENCE TO RELATED APPLICATIONS

This application claims priority on U.S. Provisional Application Ser. No. 62/984,839, filed on Mar. 4, 2020, the disclosures of which are incorporated herein by reference.

FIELD OF THE INVENTION

This disclosure relates generally to orthopedic devices, and more particularly to a brace that may be used on either of a wearer's left-hand and right-hand, and which provides enhanced support for the thumb.

BACKGROUND OF THE INVENTION

Wrist braces may be worn for many different reasons. A wrist brace may be worn to protect the wrist against injury during strenuous activity, such as during sporting events (e.g., hockey, gymnastics, golf, tennis, etc.) or while lifting heavy objects. A wrist brace may also be worn to help rehabilitate an injury of the wearer's wrist, which may be a traumatic injury (acute injury) or an overuse (chronic injury). Typical traumatic injuries requiring use of a wrist brace may include, but are not limited to, sprains, torn ligaments, joint dislocations, muscle strains, broken bones, etc. Typical overuse injuries to the wrist may include, but are not limited to, inflamed tendons, carpal tunnels syndrome, wrist sprains, dislocations, nerve injuries, stress fractures, etc.

Some early wrist support devices are shown, for example, by U.S. Pat. No. 4,441,490 to Nirschl; U.S. Pat. No. 4,850,309 to Elsey; and U.S. Pat. No. 5,267,943 to Dancyger. More recent wrist support devices are shown, for example, by U.S. Pat. No. 7,824,352 to Jaccard; U.S. Pat. No. 8,147,438 to Livolsi; and U.S. Pat. No. 9,872,792 to Romo.

The herein disclosed apparatus provides improvements to wrist braces.

It is noted that citing herein of any patents, published patent applications, and non-patent literature is not an admission as to any of those references constituting prior art with respect to the herein disclosed apparatus.

OBJECTS OF THE INVENTION

It is an object of the invention to provide a brace that may be used to secure a wrist of a wearer against movement to enable healing and prevent further injury.

It is another object of the invention to provide an ambidextrous wrist brace, being easily and rapidly converted from a configuration that is usable on the wearer's left hand to a configuration that is usable on the wearer's right hand.

It is a further object of the invention to provide a wrist brace that provides improved support for the thumb of the wearer.

It is another object of the invention to provide a wrist brace that may immobilize the thumb of the wearer.

Further objects and advantages of the invention will become apparent from the following description and claims, and from the accompanying drawings.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A first embodiment of a wrist brace may be configured for alternate use on each of a right hand and a left hand of a wearer. The wrist brace may include: a casing, a pull tab, at least two elastic securing members, a center stay, a thumb support member, and a flap.

The casing may be formed of a flexible material and may have a quadrilateral shape when in a flattened condition, with first and second ends, and distal and proximal ends being symmetric about a center axis. The casing may be formed to include a first thumb socket usable for the right hand and a second thumb socket usable for the left hand, each of which may be formed in proximity to the proximal end, and each of which may be positioned symmetrically with respect to the center axis, and may be formed with a continuous periphery configured to completely surround the thumb of the wearer when inserted therethrough. Each thumb socket may be reinforced, and may be an oval-shaped opening. The casing may be formed to include: first, second, and third elongated pockets. The first elongated pocket may be formed parallel to the center axis to extend between the first thumb socket and the distal end, with an opening formed into the first elongated pocket. The second elongated pocket may be formed parallel to the center axis to extend between the second thumb socket and the distal end, with an opening formed into the second elongated pocket. The third elongated pocket may be formed to be substantially centered with respect to the center axis, extending between the proximal end and the distal end. A center stay may be positioned within the third elongated pocket. The casing may also be formed to include at least two holes, each of which may be formed in proximity to the first end of the casing, and each hole may be reinforced, e.g., using a grommet.

The at least two elastic securing members may be positioned to pass through a respective one of the at least two holes, and each of the at least two elastic securing members may have a respective first end fixedly secured to the pull tab, and a respective second end fixedly secured proximate to the second end of the casing.

The thumb support member may be formed to include: a loop-type fabric material; a strap, and a thumb stay fixedly secured to the loop type fabric material. The thumb stay may be configured to be received within either of the first and second elongated pockets for respective use on the right hand and left hand. The strap may have a first end fixedly secured to the loop type fabric, and may have hook-type material on a second end thereof. The flap is configured to releasably secure the thumb support member to the casing. The releasable securement of the flap permits adjustments to a position of the elongated stay of the thumb support member within either of the first and second elongated pockets. In one embodiment, a first end of the flap is fixedly secured to the casing, and the second end of the flap is configured for the releasable securement using the hook type and the loop type materials. In another embodiment, a first end of the flap is also releasably secured to the casing.

The strap may be configured to loop around a thumb of the wearer and releasably secure to the casing using the hook-type material on the strap. The length of the strap may also be configured to loop around the thumb of the wearer and releasably secure to the casing and to the flap using the hook-type material and the loop-type material to redundantly secure the thumb support member. The strap may also be formed with a length configured to loop only once around the wearer's thumb to support the wearer's thumb, or alternatively may have a length configured for the strap to loop twice around the wearer's thumb to immobilize the wearer's thumb.

A second wrist brace embodiment may also be configured for alternate use on each of a right hand and a left hand of a wearer. This wrist brace may include: a casing, a pull tab, at least two elastic securing members, a center stay, a thumb stay, and a strap. The casing and this brace overall may be formed similar to that of the first brace embodiment, although it does not include the detachable thumb support member. A thumb stay is configured to be received within either of the first and second elongated pockets for respective use on the right hand and left hand, through respective openings that may be formed proximate to the distal end of the casing. The strap may be configured to loop around a thumb of the wearer, with each of a first end and a second end of the strap being releasably secured to the casing.

BRIEF DESCRIPTION OF THE DRAWINGS

The description of the various example embodiments is explained in conjunction with appended drawings, in which:

FIG. 9 is the front view of the rounded configuration of the flexible casing, elastic securing members, pull tab, and flaps, as shown in FIG. 7, but is also shown with the thumb support member of FIG. 8 just prior to insertion of its stay into the pocket exposed by the drawn back pull tab;

FIG. 30 is a front view of the thumb support member shown in FIG. 28;

FIG. 31 is a front view of the thumb stay pocket member shown in FIG. 28;

FIG. 32 is a front view of the thumb stay pocket cover shown I FIG. 28;

FIG. 33 is a front view of the thumb stay shown in FIG. 28;

FIG. 34 is a side view of the thumb stay of FIG. 31;

FIG. 35 is a front view of the dorsal wrist stay pocket member shown in FIG. 28;

FIG. 36 is a front view of the dorsal wrist stay pocket cover shown in FIG. 28;

FIG. 37 is a front view of the dorsal wrist stay shown in FIG. 28;

FIG. 38 is a side view of the dorsal wrist stay of FIG. 37;

FIG. 39 is a front view of the elastic fabric connector member;

DETAILED DESCRIPTION OF THE INVENTION

Figure 1:
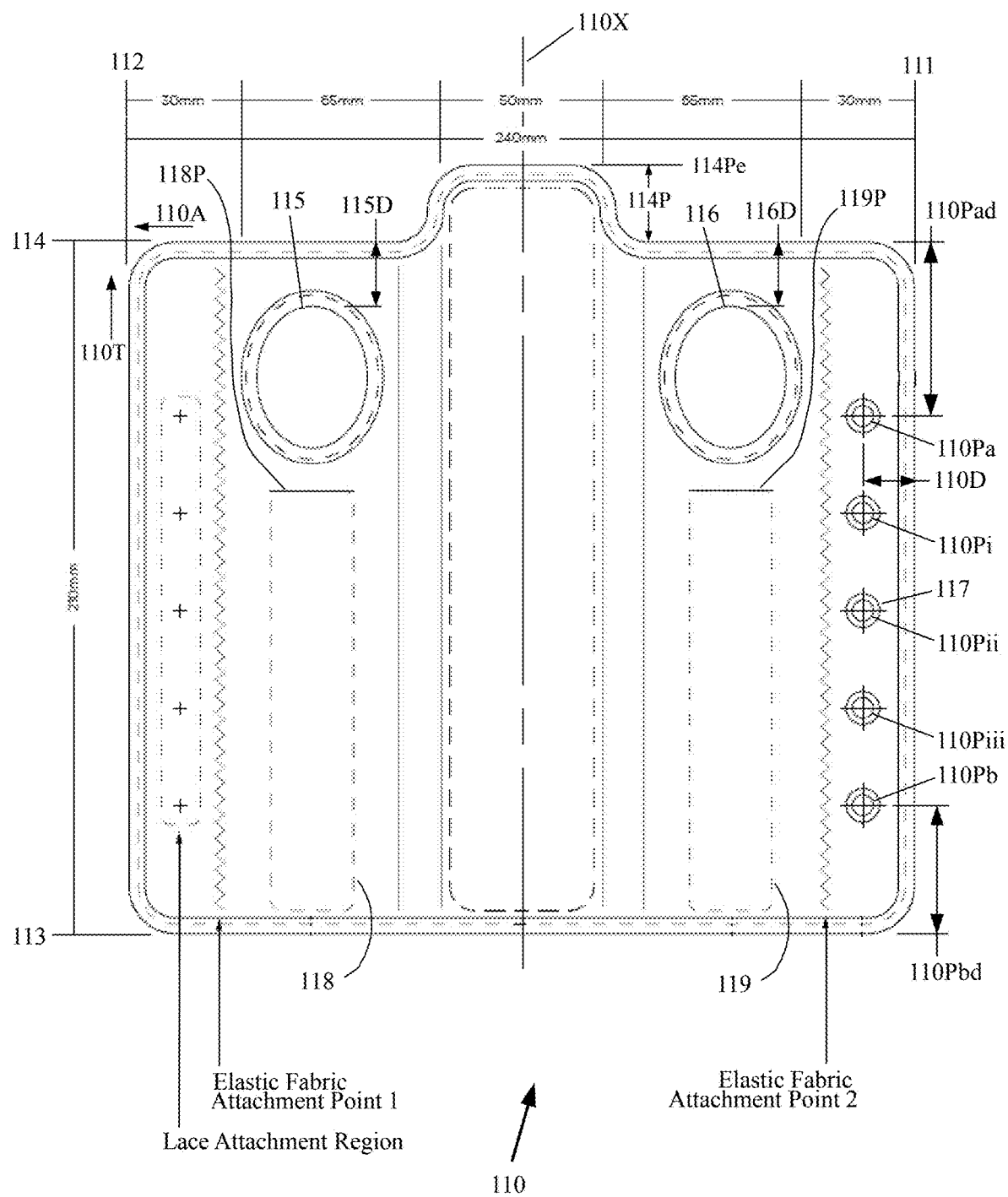
FIG. 1 is a front view of the flexible casing of the wrist brace disclosed herein, shown in a flattened configuration.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed and/or claimed apparatus/method.

Furthermore, the reference throughout this specification to "one embodiment" or "an embodiment" means that a particular feature, structure or characteristic described in connection therewith is included in at least that one particular embodiment. Thus, the appearances of the phrases "in one embodiment" or "in an embodiment" in various places throughout this specification are not necessarily all referring to the same embodiment. Additionally, the described features, advantages, and characteristics of any particular embodiment disclosed herein may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculators/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit, and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipedia.org/wiki/Engineering_fit; and "Three General Types of Fit," available at www.mm-to.org/dclark/Reports/Encoder%20Upgrade/fittolerences%20%5BRead-Only%5D.pdf.

The terms "rigid," and "flexible," and "resilient" may be used herein to distinguish characteristics of portions of certain features of the wrist brace. The term "rigid" indicates that an element is devoid of flexibility such that it does not readily lose its overall shape when force is applied, and in fact it may break if an attempt to bend it is made with sufficient force. The term "flexible" indicates that the element is capable of repeated bending such that it may be bent into different shapes and does not retain a general shape, but instead readily deforms when force is applied. The term "resilient" indicates that the element has such flexible features and also has a tendency to return to its initial general shape without permanent deformation once a force that causes such flexure is removed. The term "semi-rigid" indicates that the element may have some degree of flexibility or resiliency.

It is further noted that any use herein of relative terms such as "top," "bottom," "upper," "lower," "vertical," and "horizontal" are merely intended to be descriptive for the reader, and may be based on the depiction of those features within the figures for one particular position of the brace, and such terms are not intended to limit the orientation with which the disclosed brace may be utilized.

Figure 2:
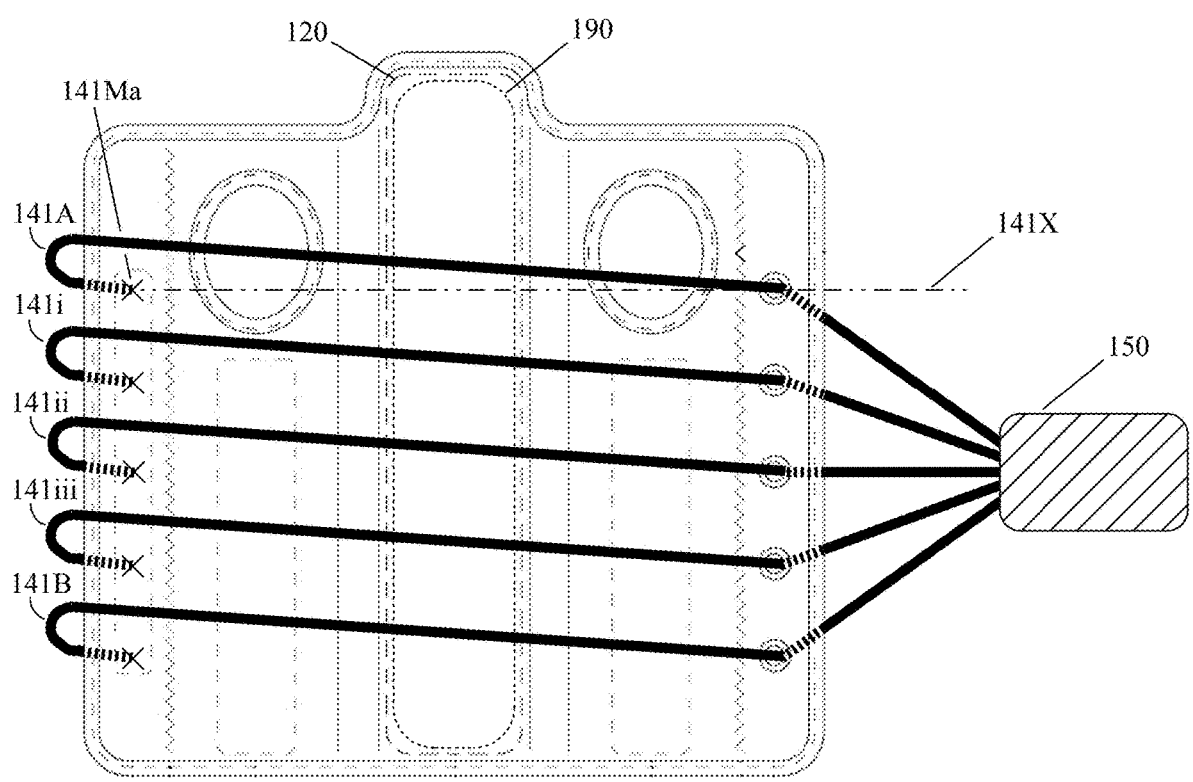
FIG. 2 is the front view of the flexible casing of FIG. 1, but shown with a plurality of elastic laces having a first end secured to the casing, and with a second end having been respectively fed through an opening of the casing with a grommet, before being secured to a pull tab.
Figure 12:
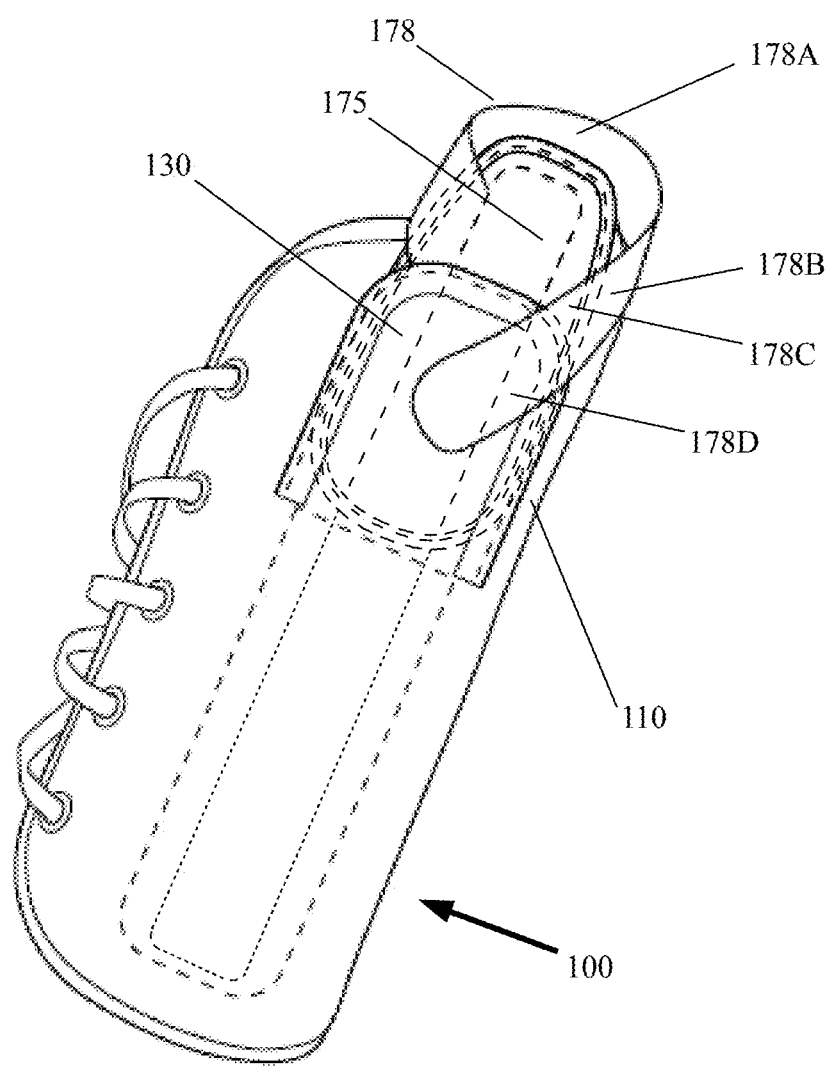
FIG. 12 is the front view of FIG. 11, but is shown with the thumb strap looped around to have its distal end releasably secured to the fabric material attached to the stay of the thumb support member.
Figure 13:
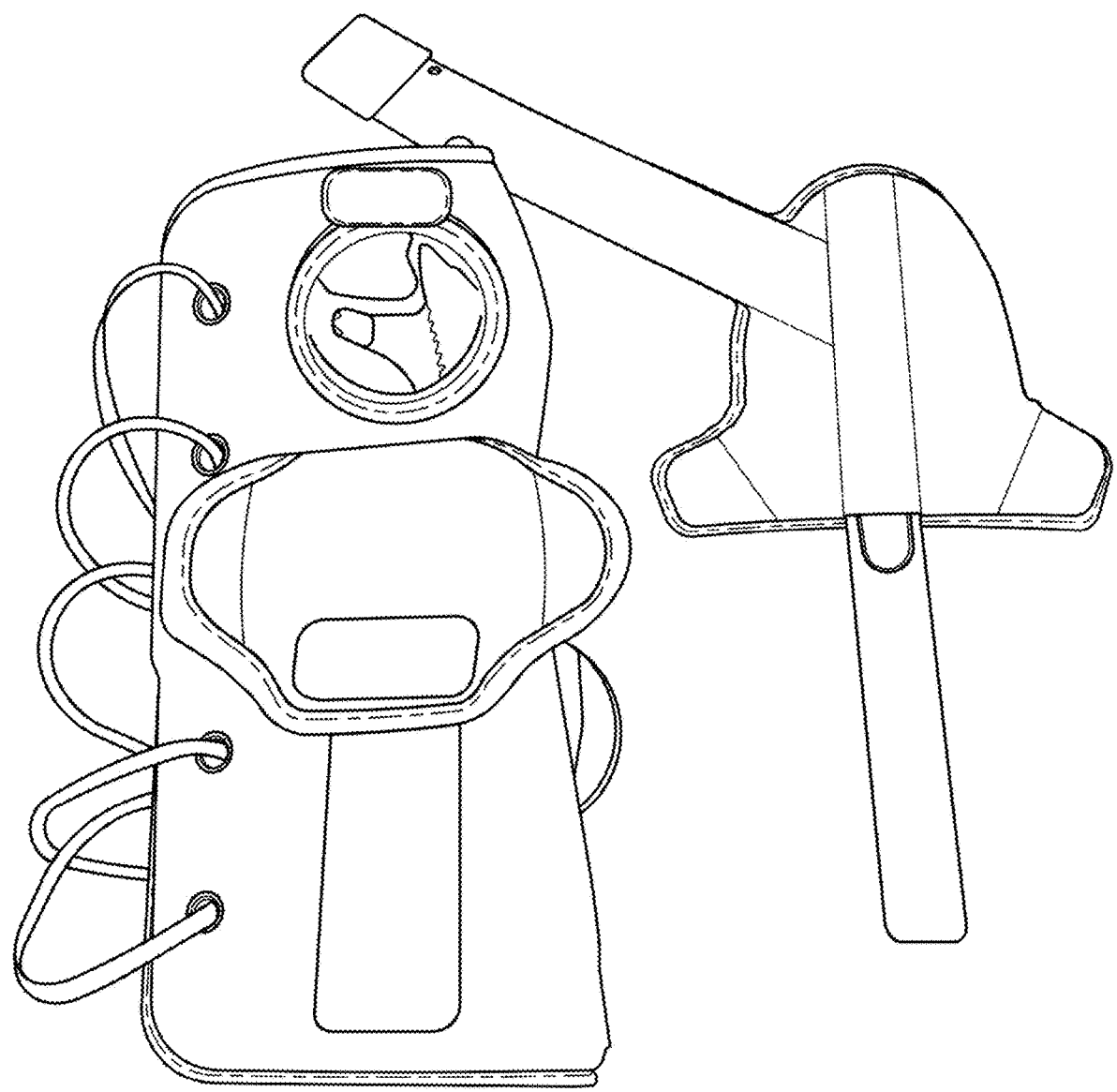
FIG. 13 is a photographic image of a front view of another embodiment of the wrist brace disclosed herein, shown prior to inserting of the thumb support member into the pocket.
Figure 13A:
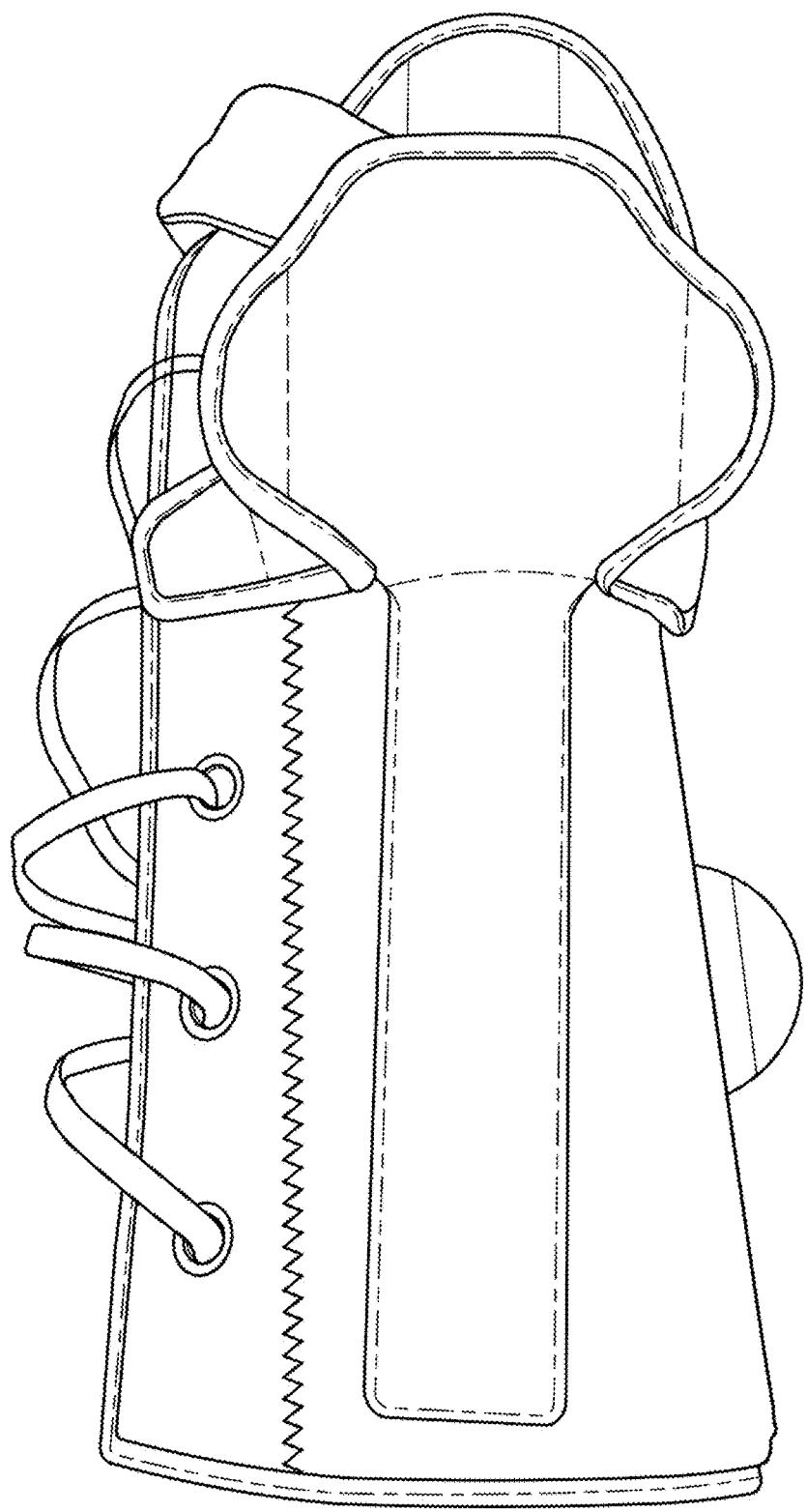
FIG. 13A is a photographic image of the wrist brace embodiment of FIG. 13, shown after inserting of the thumb support member into the pocket.

An ambidextrous wrist brace 100 is shown in FIG. 2 and FIG. 12, and may broadly include a flexible casing 110; at least one flap 130; a plurality of elastic securing laces (e.g., 141A and 141B, as well as 141*i*, 141*ii*, and 141*iii* where a corresponding plurality of openings are used in the casing); a pull tab 150; and a thumb support member 170.

The flexible casing 110 of the ambidextrous wrist brace 100 is shown in a flattened condition in FIG. 1. The flexible casing 110 may have a four-sided (i.e., quadrilateral) shape (e.g., rectangular) in the flattened condition that may extend between a first end 111 and a second end 112 in an axial direction 110A, and may extend between a distal end 113 and a proximal end 114 in a transverse direction 110T. The ends 111 and 112 may be formed to be parallel to each other, and the ends 113 and 114 may also be formed parallel to each other. The ends 111/112 may be formed to be substantially perpendicular to the ends 113/114, to form a substantially rectangular-shaped periphery for the flexible casing 110. Alternatively, the ends 111/112/113/114 may be oriented differently to form other general shapes, including, but not limited to, a trapezoidal shape, which may accommodate a wearer that has a large (muscular) forearm, which trapezoidal shaped casing 110 may form a generally conical brace rather than a generally cylindrical brace (see FIG. 6).

The periphery of the flexible casing 110 on the proximal end 114 may be formed with a protrusion 114P that may protrude symmetrically with respect to the center axis 110X, and which may terminate at end 114Pe, as seen in FIG. 1.

The flexible casing 110 may be made of any suitable material, and is preferably made of one or more layers of a breathable and flexible material. The casing material may include, but is not limited to, a hypoallergenic/moisture-wicking material (which may be disposed to face and contact the wearer's skin), any suitable soft good material that may be woven (i.e., using nylon, cotton, etc.) or non-woven, such as felt, velvet, or an open-cell plastic foam, a polyurethane film (which may be used as an outer layer), hook type material and loop type materials-which are descriptive names for such materials sold under the trademark VELCRO®, (which may be used on the outermost layer, and may preferably be the loop-type material used thereat), etc. Where multiple layers are utilized they may be bonded and/or laminated together, and/or may be joined together using any other suitable process known in the art. The hook type and loop type materials may also be used on portions of the outer layer, as discussed hereinafter.

The raw material used to make the casing 110 may be folded over and/or be stitched at its periphery to form the ends 111/112/113/114 to prevent fraying, or alternatively the rough shaped raw material used to make the casing 110 may have a narrow width tape stitched along its periphery to prevent fraying, which may similarly be done for any openings formed therein.

As seen in FIG. 1, the casing 110 may be formed with a pair of openings that form a first thumb socket 115 and a second thumb socket 116, each of which may be formed in general proximity to the proximal end 114, being separated therefrom by a small distance (i.e., distance 115D and 116F, where distance 115D may be substantially the same as distance 116D). Each of the first thumb socket 115 and second thumb socket 116 may also be formed the same distance away from the center axis 110X, so that the sockets are formed symmetrically with respect to the center axis. Each of the first thumb socket 115 and second thumb socket 116 may also be sized to receive a wearer's thumb therethrough, and may be formed with a continuous periphery configured to completely surround the thumb of the wearer when inserted therethrough. Each of the openings 115 and 116 may be formed as a circular opening to create the thumb socket; however each is instead more preferably formed as an oval shaped opening, with an axial direction of the oval shape oriented parallel to a center axis of the casing, as shown in FIG. 1, to better accommodate the shape of the portion of the thumb that will be received therein, in accordance with the angular orientation of the socket of the casing when the brace is positioned on the wearer's hand. Each of the first thumb socket 115 and second thumb socket 116 may also be formed to be slightly oversized with respect the anticipated thumb sizes for the wrist of different sized (percentile) wearers with different sized wrists/thumbs, for which different sized braces may be created and utilized, such as, but not limited to, a small size, a medium size, a larger size, etc., in which those sockets may be sized differently for the different sized wearers.

At least two small-sized openings (e.g., holes 110Pa and 110Pb) may be formed in proximity to the first end 111 of the flexible casing 110, being separated therefrom by a small distance 110D to protected against a pullout failure of the casing material, which openings may respectively receive one of the elastic securing laces therethrough. Additional openings (e.g., holes 110Pi, 110Pii, and 110Piii) may be equally spaced between the holes 110Pa and 110Pb. To further protect the material against tearing at those holes resulting from pulling on the elastic laces, a grommet 117 may be secured to each of the openings, which grommets may be made of any suitable material known in the art, including, but not limited to, plastic, metal, etc. The opening 110Pa may be formed in general proximity to the proximal end 114, being separated therefrom by a distance 110Pad, which distance may accommodate the lacing passing therethrough, while the brace is worn, to be at a point distal from the end of the thumb, being in proximity to, or beyond the base of the first metacarpal bone. The opening 110Pb may be formed in proximity to the distal end 113, being separated therefrom by a distance 110Pbd.

The flexible casing 110 may be formed with a first elongated pocket 118 formed parallel to the center axis 110X to extend between the first thumb socket 115 and the distal end 113, with an opening 118P into the pocket being formed at the end of the pocket being in proximity to the first thumb socket.

The flexible casing 110 may also be formed with a second elongated pocket 119 formed parallel to the center axis 110X to extend between the second thumb socket 116 and the distal end 113, with an opening 119P into the pocket being formed at the end of the pocket being in proximity to the second thumb socket.

The flexible casing 110 may also be formed with a third elongated pocket 120 formed parallel to, and symmetrically about, the center axis 110X, which third pocket may be centered on the center axis 110X and may extend between the distal end 113 and the end 114P of protrusion 114 (when the protrusion is used). The third elongated pocket 120 may house and enclose an elongated stay 190 (see FIG. 2) which may be configured to overlay the dorsal side of the wearer's wrist (including the knuckles) when the brace is being worn. The third elongated pocket 120 may be sewn around the stay 190, or an opening may be formed in the pocket 120 to permit insertion and removal of the stay 190 from the pocket. Additionally or alternatively, the stay 190 (or any other stay used herein) may be formed with hook material on at least one side, permitting its releasable attachment to the loop material that may be used on the outside of the flexible casing 110.

Where only two small-sized openings are used in proximity to the first end 111 of the flexible casing 110, being the two holes 110Pa and 110Pb, the plurality of elastic securing laces utilized may be the elastic laces 141A and 141B; however, where the openings additionally include holes 110Pi, 110Pii, and/or 110Piii, elastic laces 141i, 141ii, and/or 141iii may correspondingly be utilized. Thus, the ambidextrous wrist brace 100 uses one elastic securing lace member for each of the openings formed in the casing 110.

Figure 3:
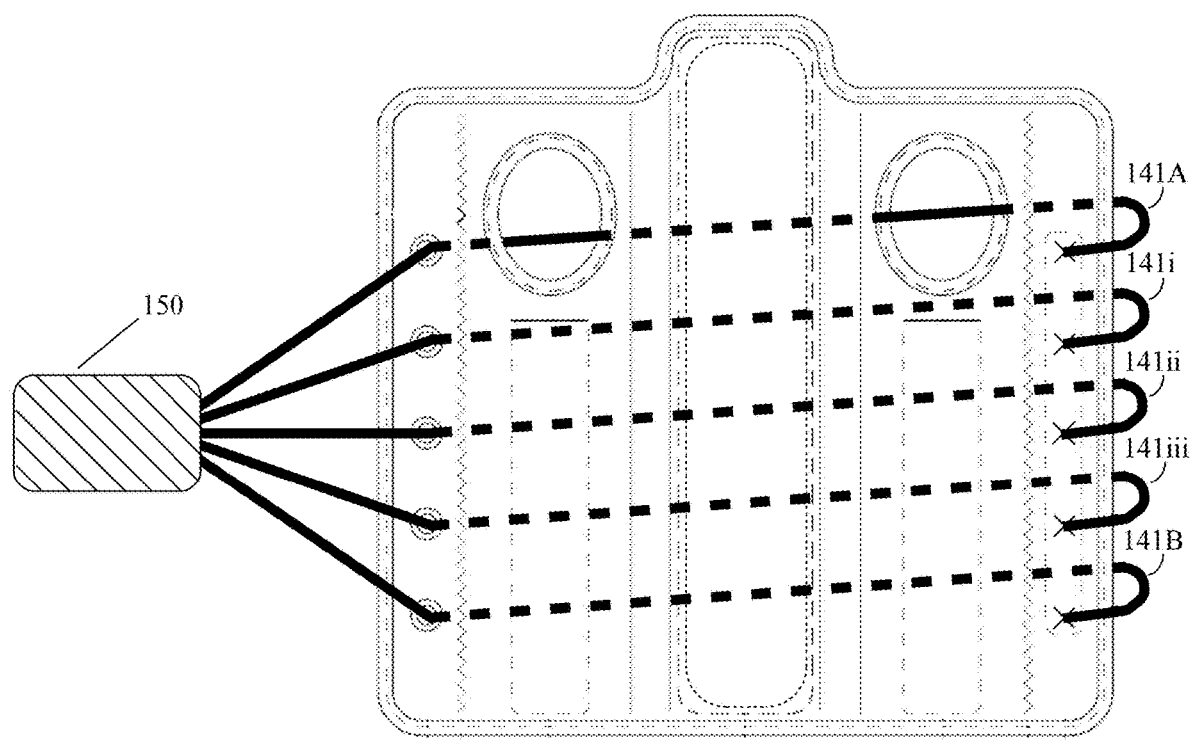
FIG. 3 is a rear view of the flexible casing, elastic securing members, and pull tab shown in FIG. 2.

Each of the elastic securing lace members (141A, 141B, 141i, 141ii, and 141iii) have a first end and a second end, with each of the first ends being fixedly secured to the pull tab 150, as seen in FIG. 2 and FIG. 3. The second end of each of the at least two elastic securing lace members (141A, 141B, 141i, 141ii, and 141iii) respectively pass through the corresponding openings (holes 110Pa, 110Pb, 110Pi, 110Pii, and 110Piii) and may be fixedly secured to the casing 114 in the attachment region shown in FIG. 1. The second end of the elastic securing lace member 141A may be fixedly secured in general proximity to the second end 112 of the flexible casing 114 and in proximity to the proximal end 114 at point 141Ma, such that a theoretical line 141X drawn between that attachment point and the hole 110Pa may be substantially parallel to the proximal end 114 (see FIG. 2). The second end of the elastic securing lace member 141B may similarly be fixedly secured in proximity to the second end of the flexible casing 114 and in proximity to the distal end 113. Where utilized, the second ends of the elastic securing lace members 141i, 141ii, and 141iii are similarly fixedly secured to the flexible casing 114, being equally spaced between the attachment points for the elastic securing lace members 141A and 141B. Note that in one embodiment of the ambidextrous wrist brace 100, the extent of the flexible casing 114 may be as dimensioned in FIG. 1, and preferably uses the five elastic securing lace members (141A, 141B, 141i, 141ii, and 141iii).

The pull tab 150 may generally be formed of the same flexible material as the casing 114; however, while the casing may be formed with a portion of its exterior having either a hook or loop type material secured thereon, one side (or both sides) of the pull tab may be formed with the other of those two materials (e.g., the hook-type material where the loop-type material is used on the outmost layer of the casing), permitting releasable attachment of the pull tab to the casing.

Figure 5:
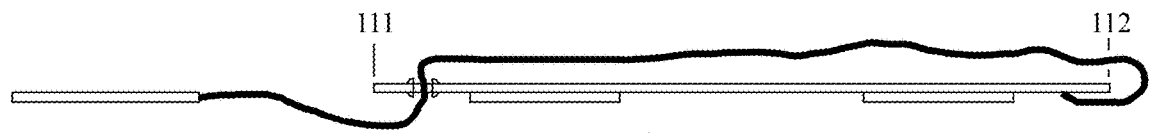
FIG. 5 is a top view of the flexible casing, elastic securing members, pull tab, and flaps, as shown in the flattened configuration of FIG. 4.
Figure 4:
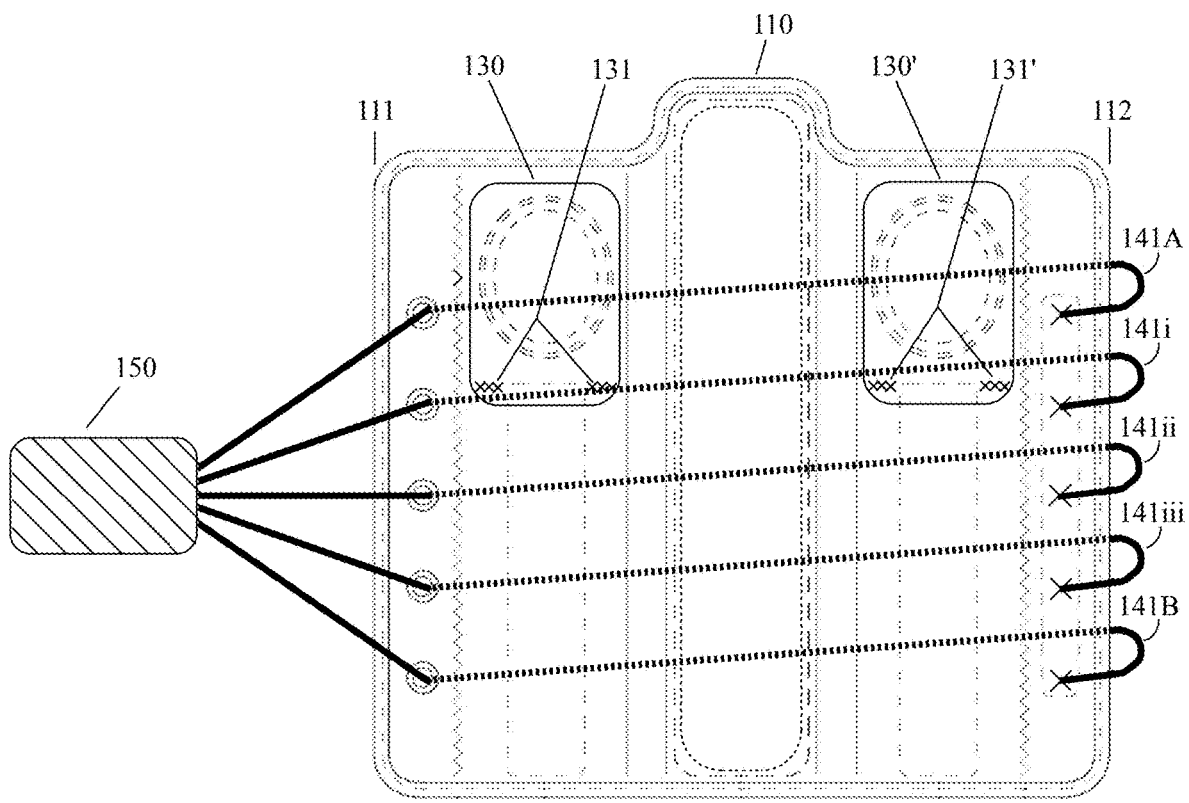
FIG. 4 is the rear view of FIG. 3, but is shown with a pair of flaps releasably secured to the flexible casing, to respectively overlie each of the two thumb sockets.
Figure 6:
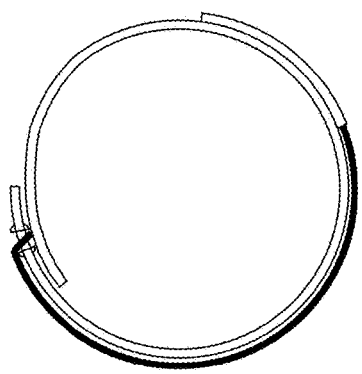
FIG. 6 is the top view of FIG. 5, but shown after the pull tab has been pulled to draw one end of the flexible casing to overlap a second end of the casing in a rounded configuration, and with the pull tab releasably secured to the flexible casing using hook and loop fastening materials.
Figure 6A:
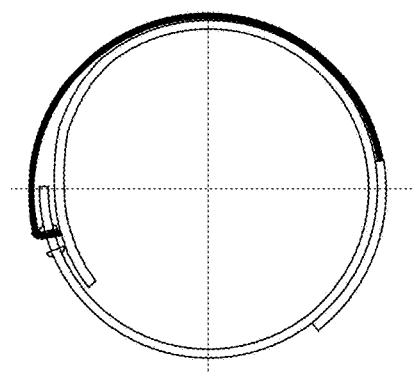
FIG. 6A is the top view of FIG. 6, but show with the pull tab having been pulled in the opposite direction before being releasably secured to the flexible casing using hook and loop fastening materials.
Figure 7:
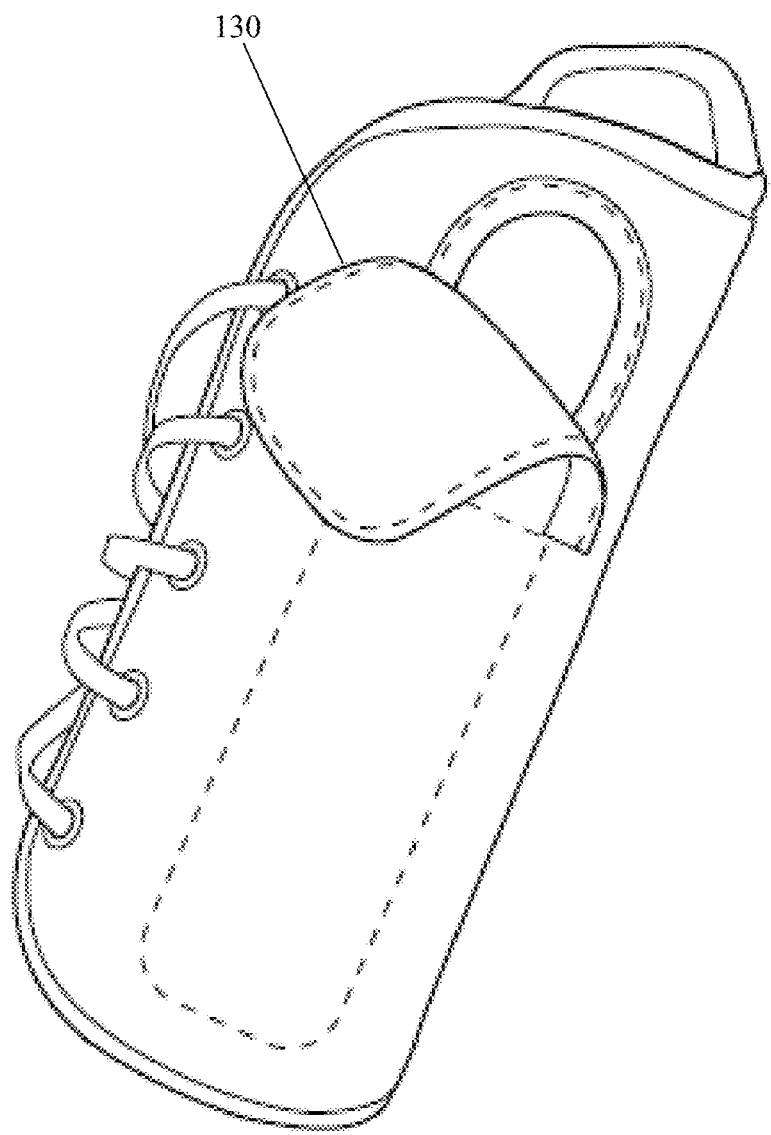
FIG. 7 is a front view of the rounded configuration of the flexible casing, elastic securing members, pull tab, and flaps, as shown in FIG. 6, but is also shown with the top of one of the flaps having been drawn away from its releasable attachment to the casing.

The pull tab 150 may be pulled relative to the casing 114 to change the flat configuration of the casing 114 shown in FIG. 4 and FIG. 5, into a generally circular configuration, whereby the elastic securing lace members (e.g., 141A, 141B, 141i, 141ii, and 141iii) pull the second end 112 of the casing into proximity to the first end 111. The pull tab 150 and elastic securing lace members (e.g., 141A, 141B, 141i, 141ii, and 141iii) may be pulled only enough so that the second end 112 approaches but does not quite reach the first end 111, remaining spaced apart therefrom. Alternatively, the pull tab 150 and elastic securing lace members may be pulled enough so that the second end 112 is aligned with the first end 111, or is positioned beyond the first end 111 for the casing to overlap upon itself, as shown in FIG. 6 and FIG. 6A. The pull tab 150 may be pulled in either a first direction, as illustrated in FIG. 6, or in a second direction, as illustrated in FIG. 6A.

As may be seen in FIG. 4 and FIG. 12, the ambidextrous wrist brace 100 may include a flap 130. The flap 130 may generally be formed of the same flexible material as the pull tab 150, and may be sized and shaped to be mounted to the casing to overlie one of the thumb sockets, as seen in FIG. 4. One portion of the flap 130 (i.e., the lower portion as illustrated in FIG. 4) may be fixedly secured to the casing at 131, while an upper portion that faces the casing (i.e., a first side) may be formed with the hook or loop material (e.g., the hook-type material where the loop-type material is used for the casing, which example is used hereinafter for simplicity-see FIG. 9), permitting its releasable attachment to the casing 114 and/or the thumb support member 170. Alternatively, the entire first side of the flap 130 may be formed of the loop material, which, when the brace 100 is used on a wearer's wrist, may permit releasable attachment of a first portion of the first side of the flap to the casing, and/ releasable attachment of a second portion of the first side of the flap to the thumb support member 170 (see FIG. 12). Where the entire first side of the flap 130 is formed with the loop material, it may be utilized over either the left or right thumb sockets, so that only one flap is required, but where the flap 130 is fixedly secured to the casing 114 to overlie one of the thumb sockets, a second flap 130' may be fixedly secured at 131' to overlie the other thumb socket. The second side of the flap(s) may be formed of a loop-type material, the same as the outermost layer of the casing 114 (see FIG. 11).

Figures 8, 8A:
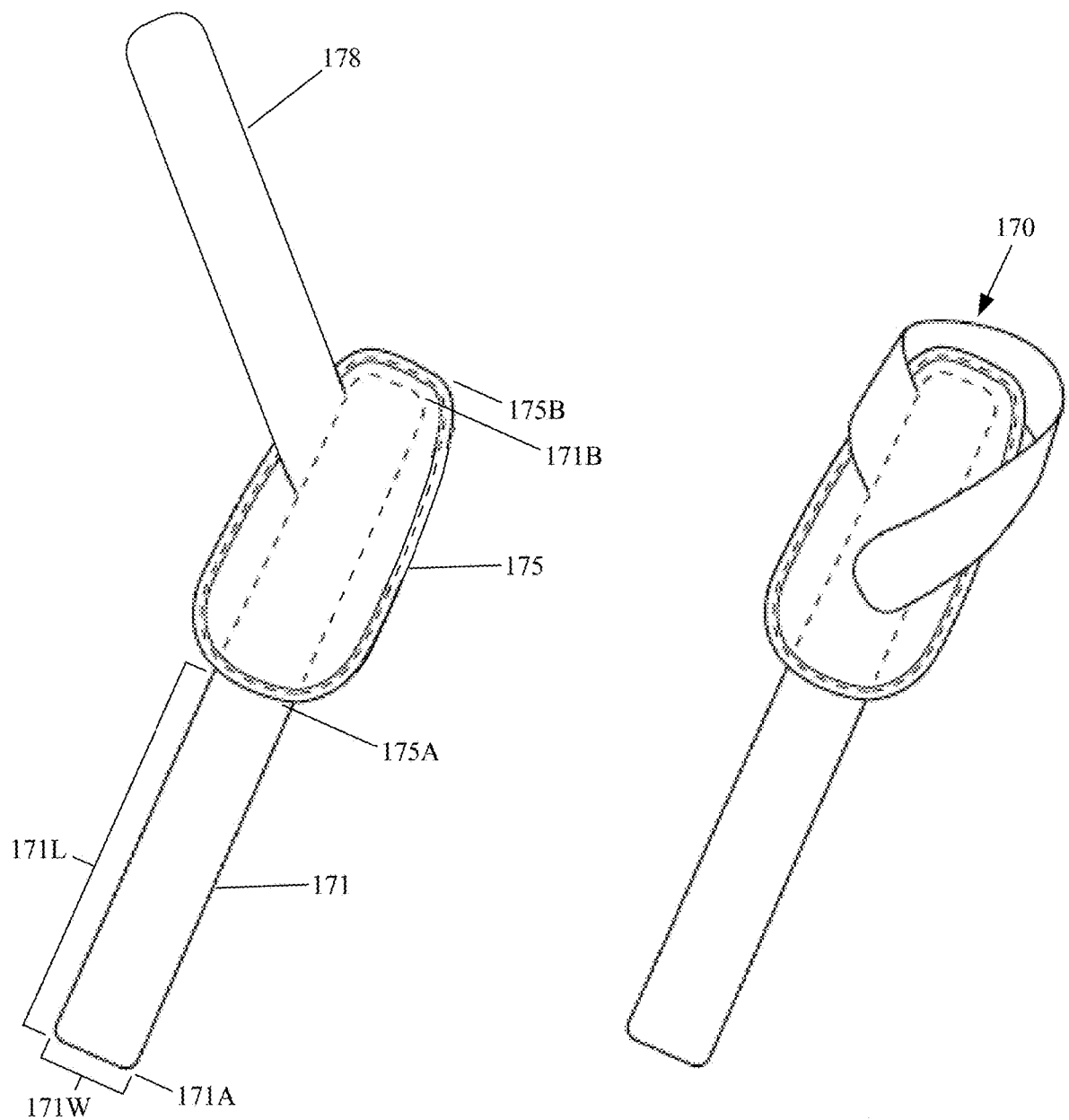
FIG. 8 is a front view of a thumb support member, shown with its thumb strap outstretched.
FIG. 8A is the front view of the thumb support member of FIG. 8, but shown with the thumb strap looped around to have its distal end releasably secured to the fabric material attached to the stay.

The thumb support member 170 may be formed of an elongated stay 171, an attachment member 175, and a strap 178. The stay 171 (and also stay 190) may each be formed of any suitably rigid material, which may include, but is not limited to, wood, plastic, metal (e.g., aluminum, steel, etc.), a composite material, etc. The stay 171 may extend from a first end 171A to a second end 171B. The attachment member 175 may extend from a first end 175A to a second end 175B, and may be fixedly secured to the stay 171 as shown in FIG. 8. The outer surface of the attachment member 175 may be formed to include a hook or loop material, the same as the casing 114 (e.g., the loop-type material), while the strap 178, which may have one end fixedly secured to either the attachment member 175 or the stay 171, may be formed to include the other of the hook or loop material that is used on the outer surface of the attachment member (e.g., it may be formed with the loop-type material-see FIG. 11). Therefore, as shown in FIG. 8A and also FIGS. 11-12, the strap 178 may be directed toward the far side of the attachment member 175 to be looped around the wearer's thumb and be releasably secured to the front side of the attachment member using the loop-type material.

Figure 10:
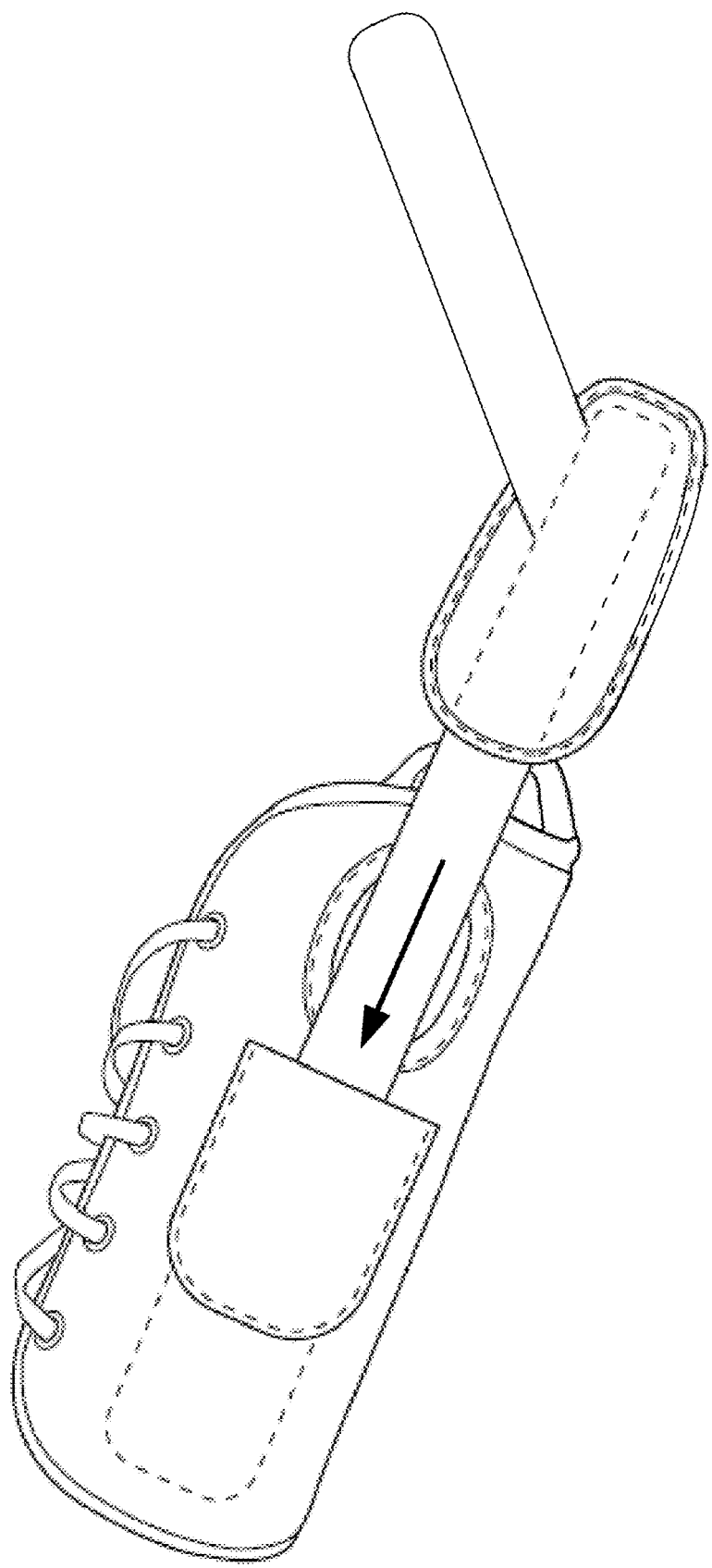
FIG. 10 is the front view of FIG. 9, but is shown with the stay of the thumb support member partially inserted into the pocket.

The width 171W of the stay 171 may permit its insertion through either of the openings 118P/119P of the pockets 118/119. The exposed length 171L of the stay 171 may permit its insertion through either of the openings 118P/119P of the pockets 118/119 (see FIGS. 9 and 10) such that the first end 175A of the attachment member 175 may be proximate to the opening (118P/119P), when the first end 171A of the stay 171 is proximate to the end of the pocket at the proximal end 113 of the casing 114, as shown in FIG. 11.

Figure 11:
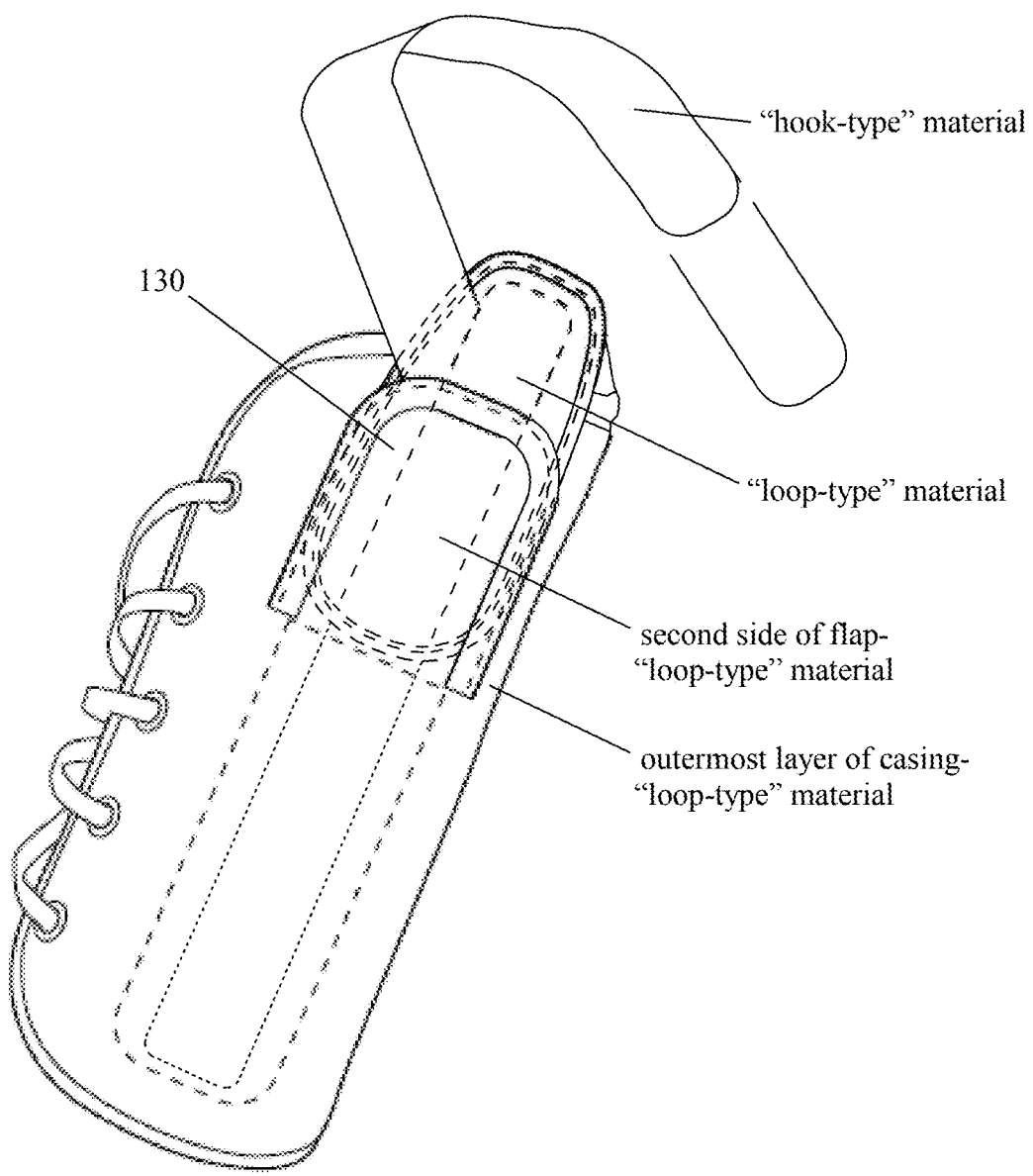
FIG. 11 is the front view of FIG. 10, but is shown with the stay of the thumb support member fully inserted into the pocket, and with the flap folded back to be releasably secured to the fabric material of the thumb support member, and with the thumb strap outstretched.
Figure 14:
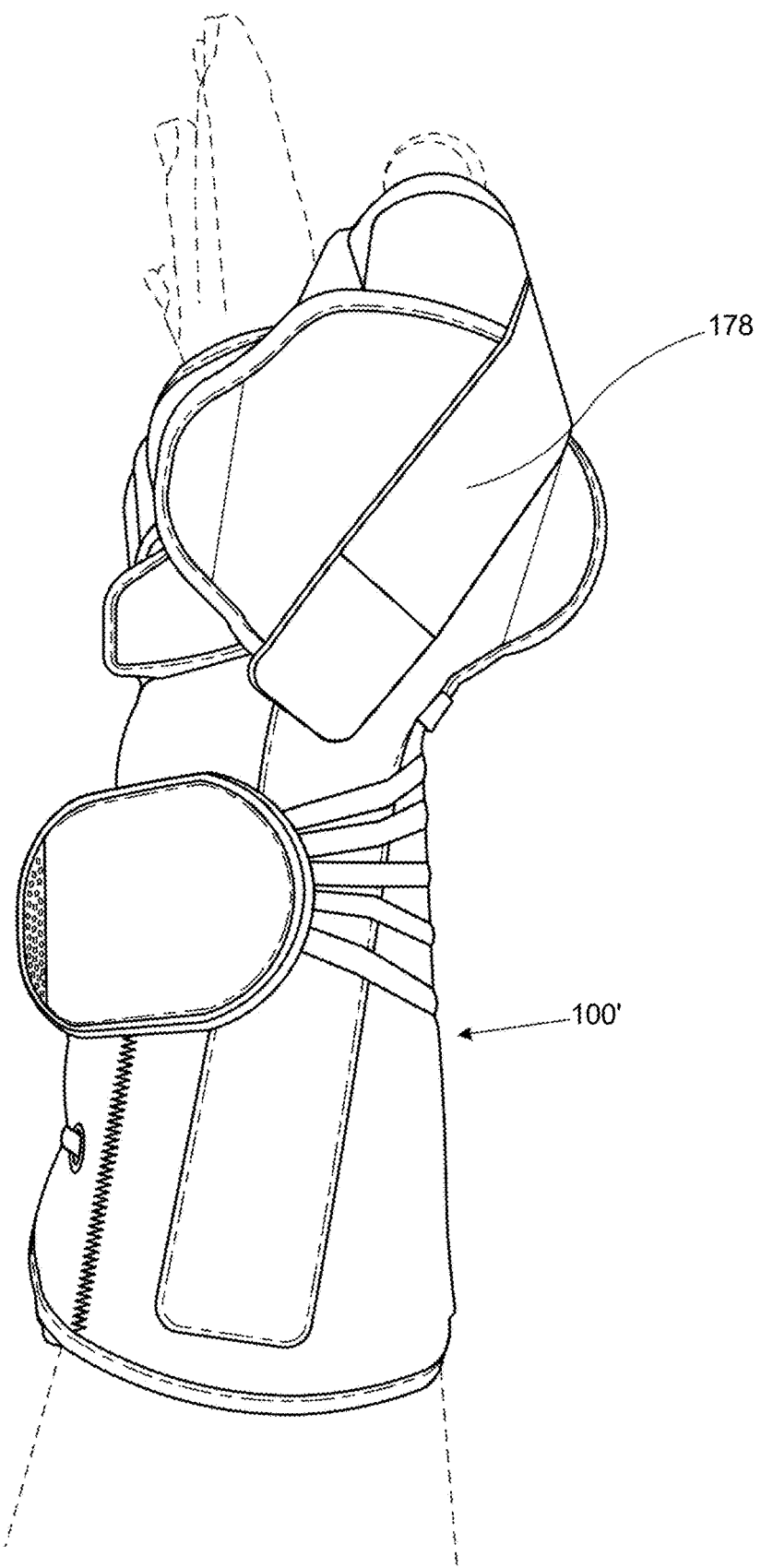
FIG. 14 is a photographic image of the front view of the wrist brace of FIG. 13, but is shown after being secured onto the left hand of a wearer.
Figure 15:
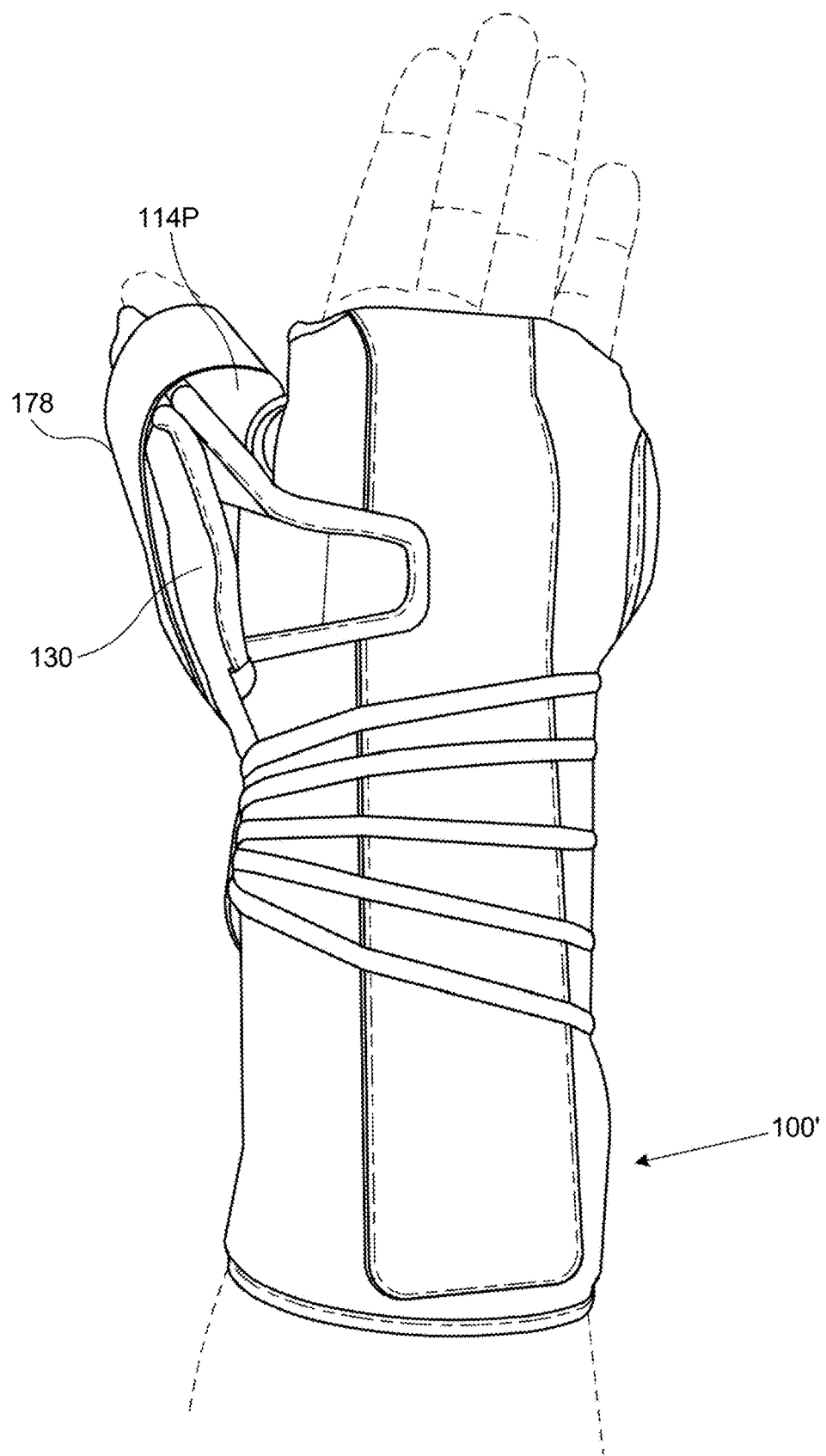
FIG. 15 is a photographic image of a side view of the wrist brace secured onto the left hand of a wearer, as shown in FIG. 14.

The first and second thumb sockets 115/116 permit ambidextrous use of the brace 100, i.e., on either the persons left or right wrist, and the stay 171 of the attachment member 170 may be inserted through the appropriate opening 118P or 119P of the pocket 118 or 119 before or after the wearer has applied the casing 114 to his/her left or right wrist, and after which the flap 130 may be releasably secured to the attachment member 175 to prevent withdrawal of the stay from the pocket, with the hook-type material on the flap being releasably secured to the loop-type material on the attachment member (se FIG. 9 and FIG. 11). Also, such releasable attachment of the flap 130 to the attachment member 175 permits subsequent adjustment to a position of the attachment member and the position of the elongated stay of the thumb support member within either of the first and second elongated pockets A wrist brace 100' that is constructed substantially similar to wrist brace 100 is shown in FIG. 14 and FIG. 15, after being secured to the wrist of the wearer's left hand.

As may be seen therein, the strap 178 of the thumb support member 170 may have a first length that generally permits looping of the strap once around the wearer's thumb, after which it may be releasably secured to at least the flap 130, as shown in FIG. 11, to support the wearer's thumb. This latter securement may redundantly prevent withdrawal of the stay from the pocket. The strap 178 may alternatively be formed with a second length being longer than the first length (see FIG. 11), that permits looping twice around the wearer's thumb before being releasably secured to the flap 130, which may tend to completely immobilize the thumb.

As may be understood from viewing FIG. 12, the hook material of the strap 178 may loop around the thumb at point 178A of the strap, and may have its hook material be releasably secured to a small portion of the casing 110 at point 178B of the strap, and/or may have its hook material be releasably secured to a small portion of the attachment member 175 at point 178C of the strap, and/or may have its hook material be releasably secured to the flap 130 at point 178D of the strap.

Figure 27:
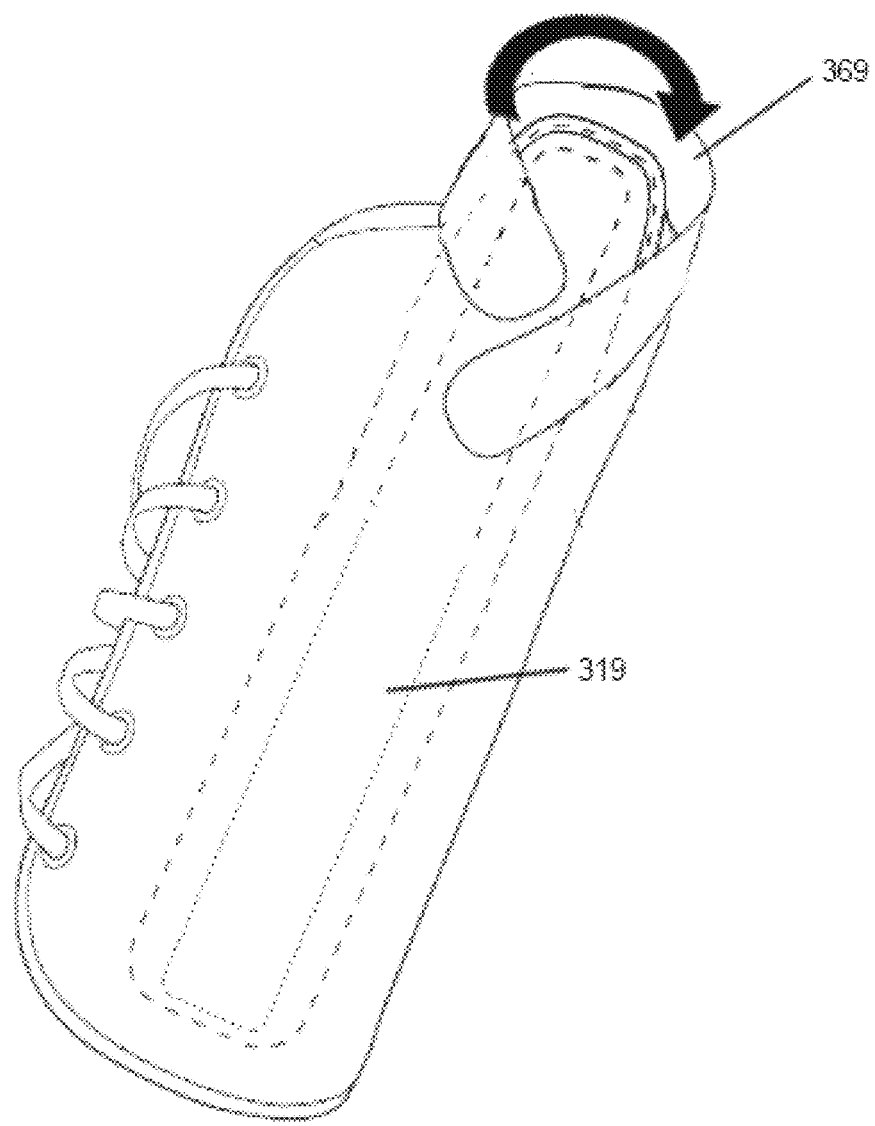
FIG. 27 is the front view of FIG. 26, but shown after the thumb strap has been wrapped around the wearer's thumb and is secured to the casing.

An ambidextrous wrist brace 300 is shown in FIG. 27, and may broadly include a flexible casing 310; a plurality of elastic securing laces (e.g., 341A and 341B, as well as 341*i*, 341*ii*, and 341*iii* where a corresponding plurality of openings are used in the casing); a pull tab 350; and a thumb support member 369.

Figure 16:
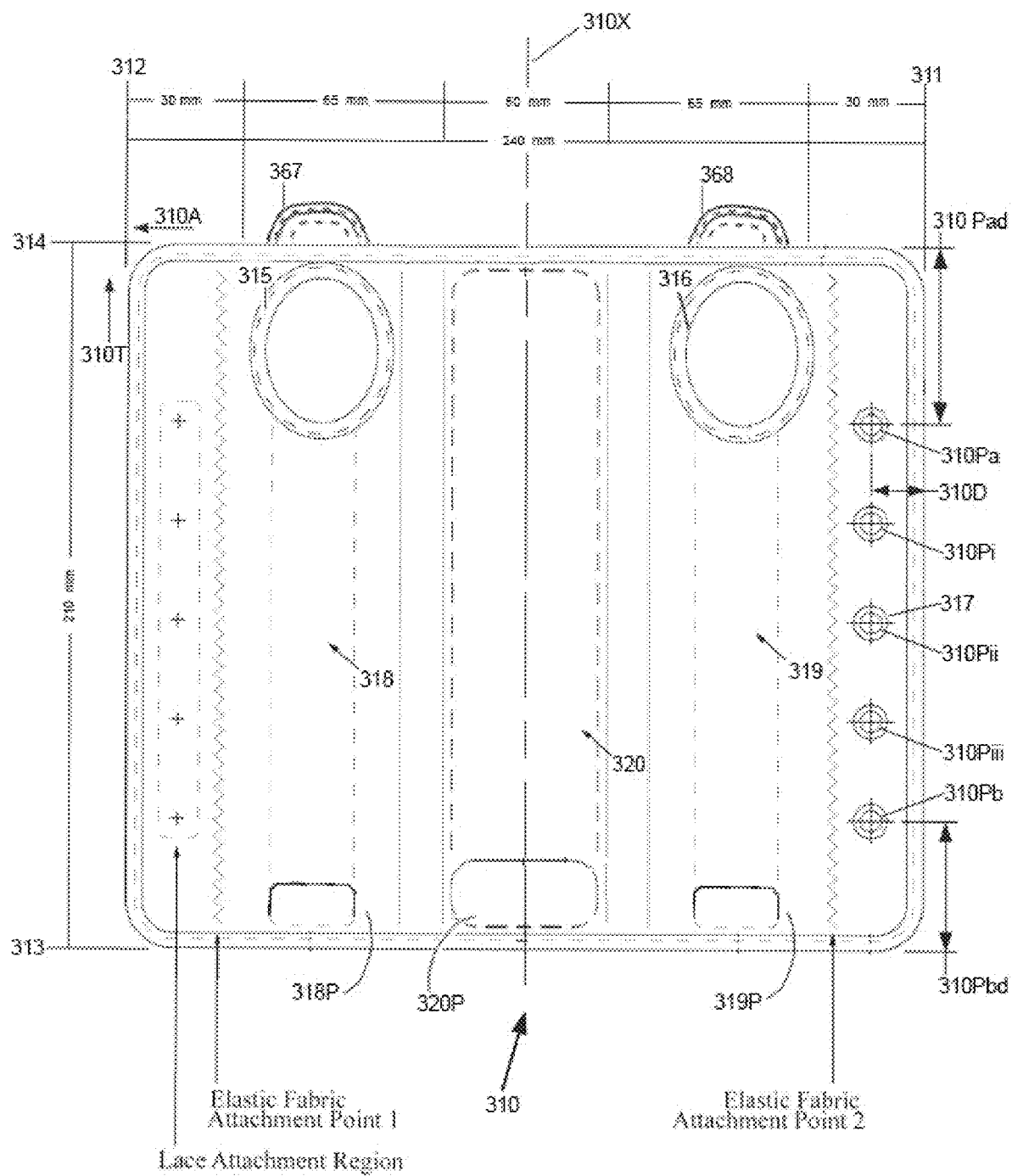
FIG. 16 is a front view of the flexible casing of another wrist brace embodiment, shown in a flattened configuration.

The flexible casing 310 of the ambidextrous wrist brace 300 is shown in a flattened condition in FIG. 16. The flexible casing 310 may extend between a first end 311 and a second end 312 in an axial direction 310A, and may extend between a distal end 313 and a proximal end 314 in a transverse direction 310T. The ends 311 and 312 may be formed to be parallel to each other, and the ends 313 and 314 may also be formed parallel to each other. The ends 311/312 may be formed to be substantially perpendicular to the ends 313/314, to form a substantially rectangular-shaped periphery for the flexible casing 310. Alternatively, the ends 311/312/313/314 may be oriented differently to form other general shapes, including, but not limited to, a trapezoidal shape, which may accommodate a wearer that has a large (muscular) forearm, which trapezoidal shaped casing 310 may form a generally conical brace rather than a generally cylindrical brace (see FIG. 21).

The flexible casing 310 may be made of any suitable material, and is preferably made of one or more layers of a breathable and flexible material. The casing material may include, but is not limited to, a hypoallergenic/moisture-wicking material (which may be disposed to face and contact the wearer's skin), any suitable soft good material that may be woven (i.e., using nylon, cotton, etc.) or non-woven, such as felt, velvet, or an open-cell plastic foam, a polyurethane film (which may be used as an outer layer), hook type material and loop type materials-which are descriptive names for such materials sold under the trademark VELCRO®, (which may be used on the outermost layer, and may preferably be the loop-type material used thereat), etc. Where multiple layers are utilized they may be bonded and/or laminated together, and/or may be joined together using any other suitable process known in the art. The hook type and loop type materials may also be used on portions of the outer layer, as discussed hereinafter.

The raw material used to make the casing 310 may be folded over and/or be stitched at its periphery to form the ends 311/312/313/314 to prevent fraying, or alternatively the rough shaped raw material used to make the casing 310 may have a narrow width tape stitched along its periphery to prevent fraying, which may similarly be done for any openings formed therein.

As seen in FIG. 16, the casing 310 may be formed with a pair of openings that form a first thumb socket 315 and a second thumb socket 316, each of which may be formed with a round or oval shape in general proximity to the proximal end 314, being separated therefrom by a small distance. Each of the first thumb socket 315 and second thumb socket 316 may also be formed the same distance away from the center axis 310X, so that the sockets are formed symmetrically with respect to the center axis. Each of the first thumb socket 315 and second thumb socket 316 may be formed as an oversized hole that may tend to accommodate most wearers, or alternatively, different sized wrist braces may be created and utilized for small, medium, and larger wearers, in which those sockets may be sized differently for the different sized wearers.

At least two small-sized openings (e.g., holes 310Pa and 310Pb) may be formed in proximity to the first end 311 of the flexible casing 310, being separated therefrom by a small distance 310D to protected against a pullout failure of the casing material, which openings may respectively receive one of the elastic securing laces therethrough. Additional openings (e.g., holes 310Pi, 310Pii, and 310Piii) may be equally spaced between the holes 310Pa and 310Pb. To further protect the material against tearing at those holes resulting from pulling on the elastic laces, a grommet 317 may be secured to each of the openings, which grommets may be made of any suitable material known in the art, including, but not limited to, plastic, metal, etc. The opening 310Pa may be formed in general proximity to the proximal end 314, being separated therefrom by a distance 310Pad, which distance may accommodate the lacing passing therethrough, while the brace is worn, to be at a point distal from the end of the thumb, being in proximity to, or beyond the base of the first metacarpal bone. The opening 310Pb may be formed in proximity to the distal end 313, being separated therefrom by a distance 310Pbd.

The flexible casing 310 may be formed with a first elongated pocket 318 formed parallel to the center axis 310X to extend between the first thumb socket 315 and the distal end 313, with an opening 318P into the pocket being formed at the bottom of the pocket and through which opening the stay is inserted, and which opening may be covered by a flap or strap that may be secured to the casing using hook and loop materials or a fastener such as a snap.

The flexible casing 310 may also be formed with a second elongated pocket 319 formed parallel to the center axis 310X to extend between the second thumb socket 316 and the distal end 313, with an opening 319P into the pocket being formed at the bottom of the pocket and through which opening the stay may be inserted, and which opening may be covered by a flap or strap that may be secured to the casing using hook and loop materials or a fastener such as a snap.

Figure 23A:
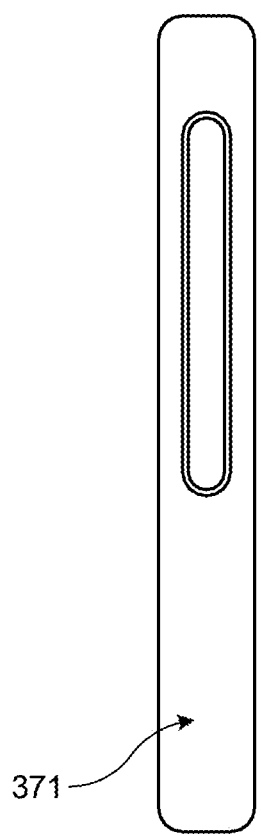
FIG. 23A is an image of a first stay that may be inserted into the pocket of the brace shown in FIG. 22.
Figure 23B:
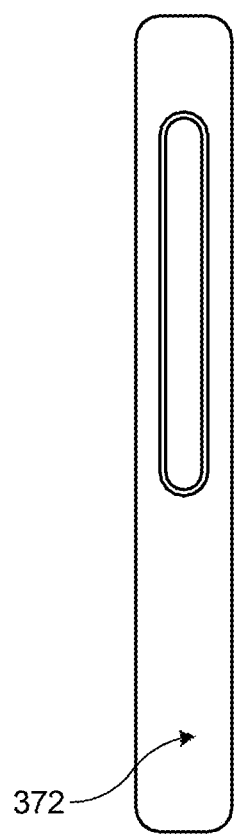
FIG. 23B is an image of a second stay that may be inserted into the pocket of the brace shown in FIG. 22.
Figure 23C:
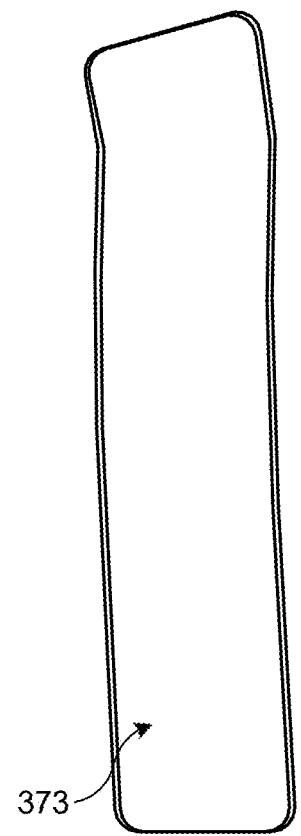
FIG. 23C is an image of a third stay that may be inserted into the pocket of the brace shown in FIG. 22.
Figure 24:
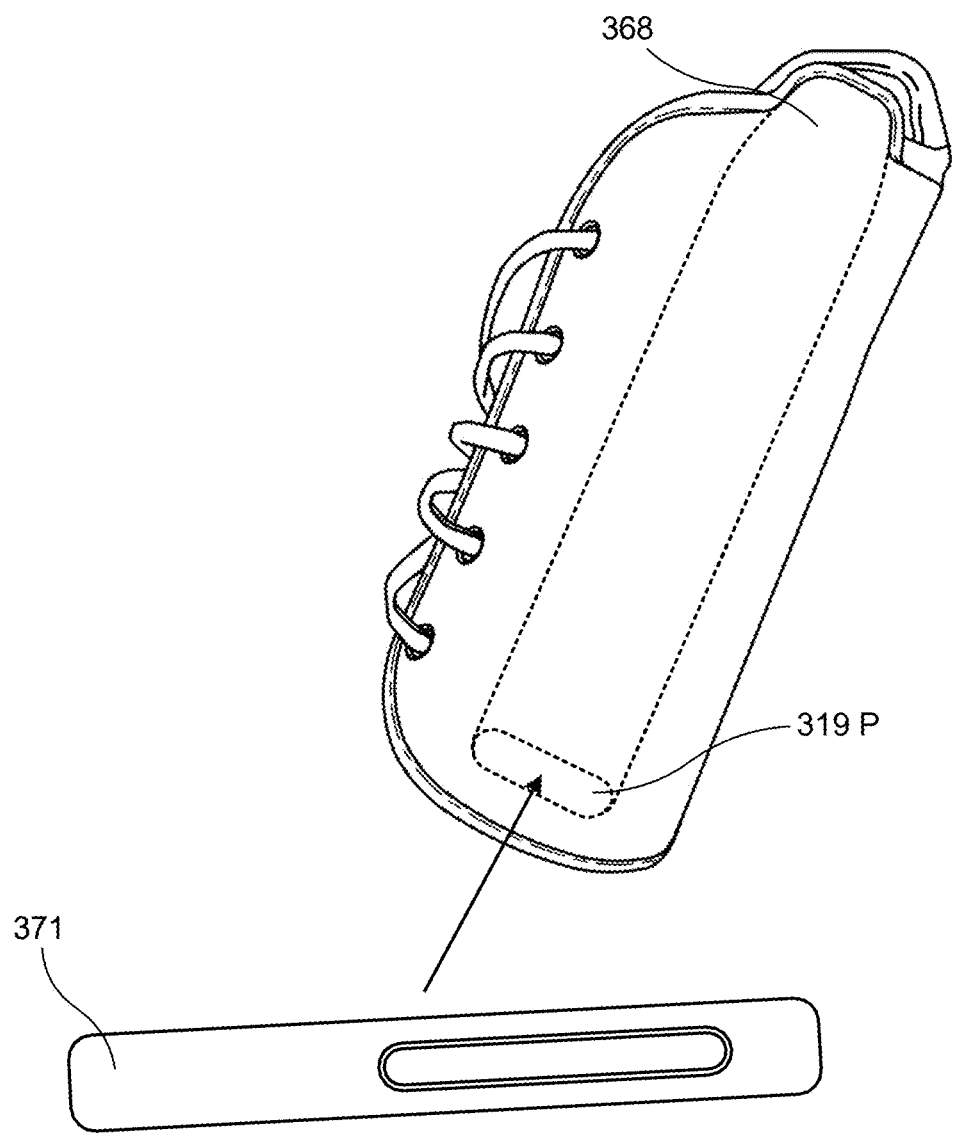
FIG. 24 is the front view of FIG. 22, showing a stay as it is initially being inserted into the bottom of the pocket.
Figure 25:
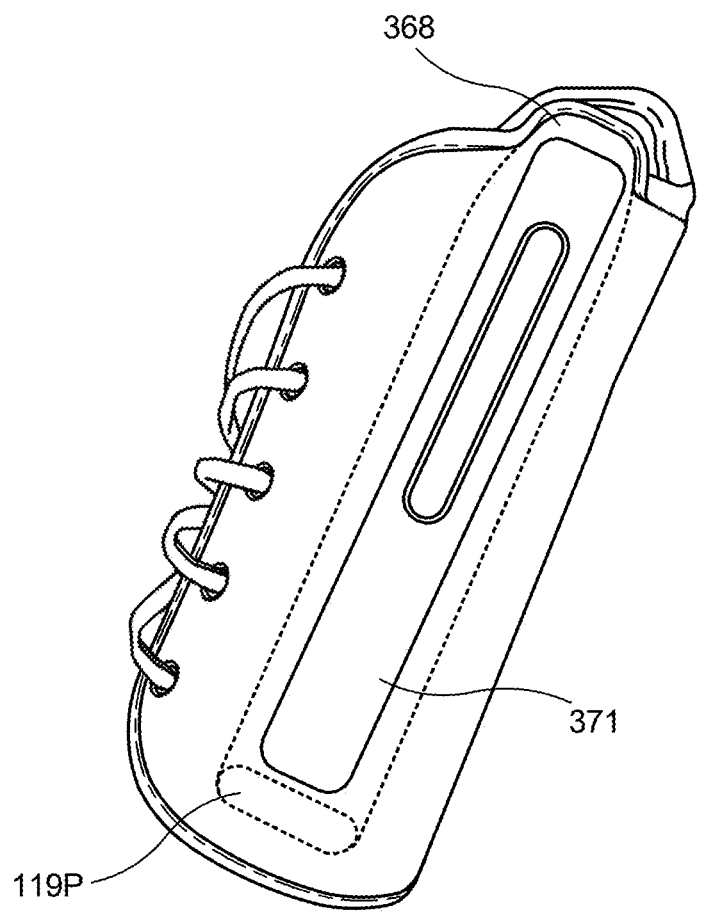
FIG. 25 is the front view of FIG. 24, but shown after the stay has been fully inserted into the pocket.
Figure 26:
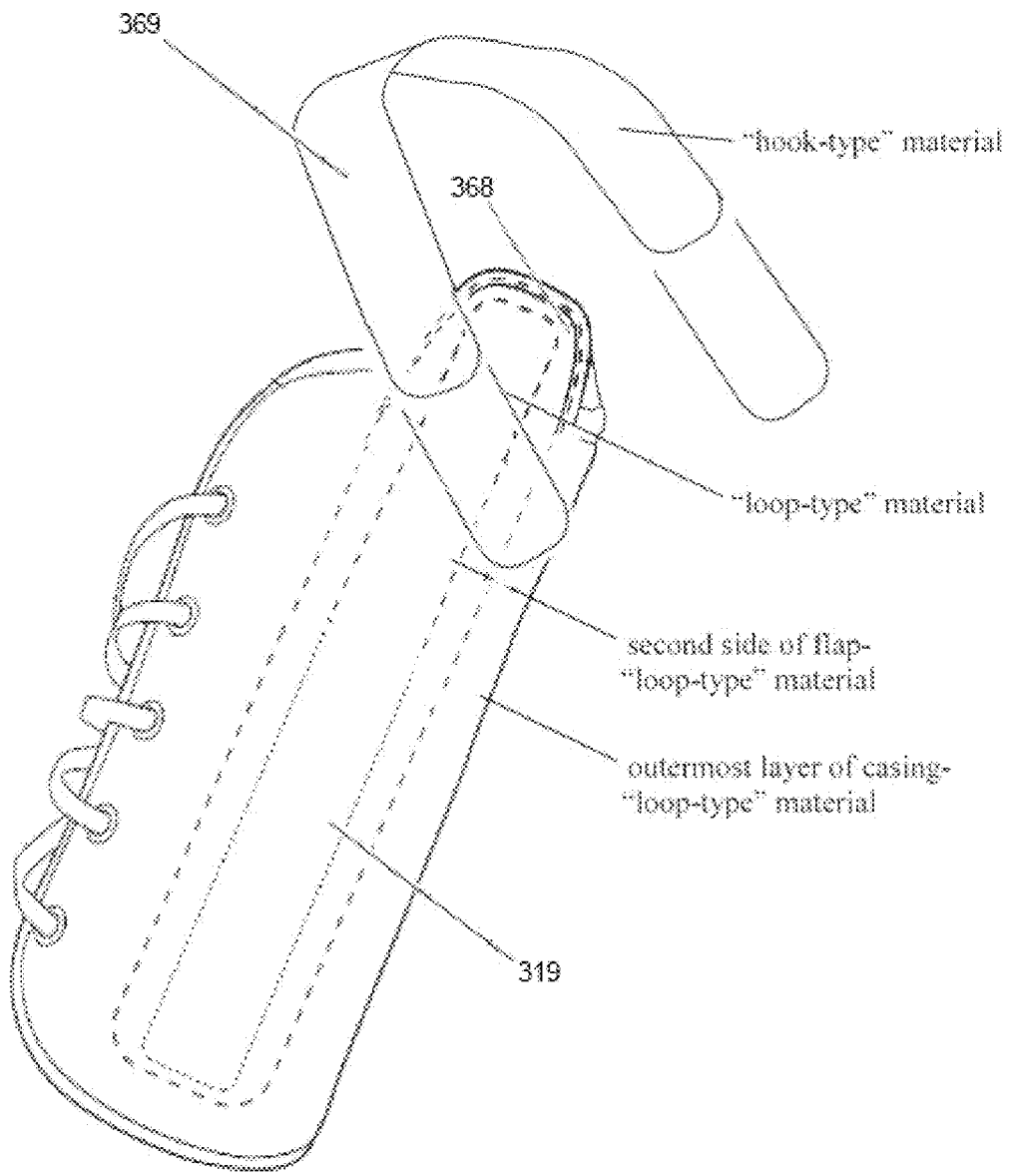
FIG. 26 is the front view of FIG. 25, but also shows attachment of the thumb strap and indication of a direction to warp the strap around the wearer's thumb.

The flexible casing 310 may also be formed with a third elongated pocket 320 formed parallel to, and symmetrically about, the center axis 310X, which third pocket may be centered on the center axis 310X and may extend between the distal end 313 and the end 314 of protrusion 314. The third elongated pocket 320 may house and enclose an elongated stay 373 (see FIGS. 23A, 23B, and 23C). The material used to form the third elongated pocket 320 may be sewn around the stay 373 and to the casing, or an opening 320P may be formed in the pocket 320 to permit insertion and removal of the stay 373 from the pocket.

Where only two small-sized openings in proximity to the first end 311 of the flexible casing 310, being the two holes 310Pa and 310Pb, the plurality of elastic securing laces utilized may be the elastic laces 341A and 341B; however, where the openings additionally include holes 310Pi, 310Pii, and/or 310Piii, elastic laces 341*i*, 341*ii*, and/or 341*iii* may correspondingly be utilized. Thus, the ambidextrous wrist brace 300 uses one elastic securing lace member for each of the openings formed in the casing 310.

Figure 17:
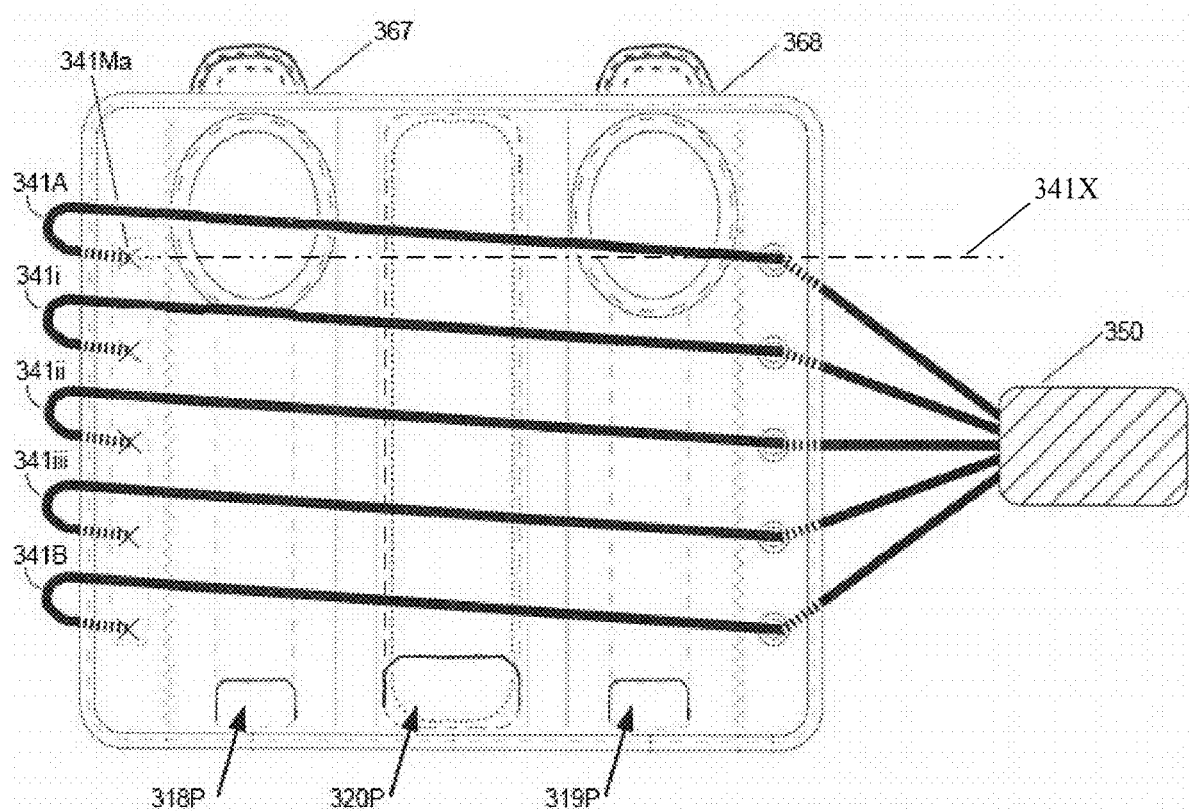
FIG. 17 is the front view of the flexible casing of FIG. 16, but shown with a plurality of elastic laces having a first end secured to the casing, and with a second end having been respectively fed through an opening of the casing with a grommet, before being secured to a pull tab.
Figure 18:
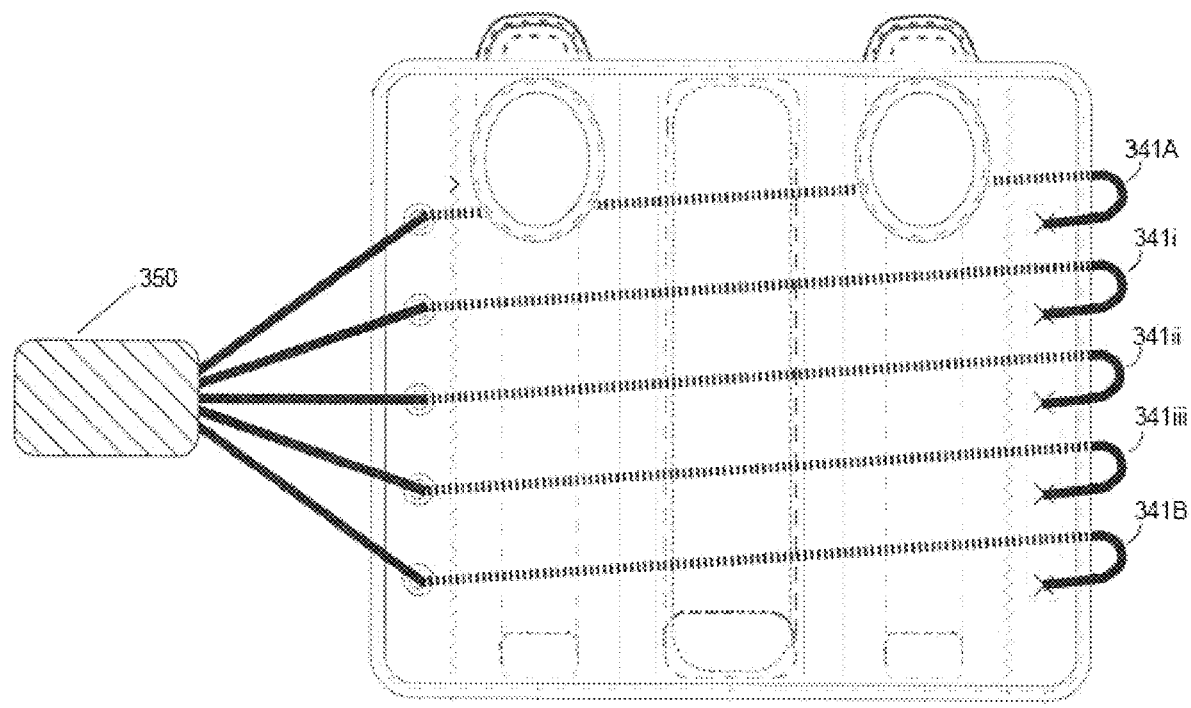
FIG. 18 is a rear view of the flexible casing, elastic securing members, and pull tab shown in FIG. 17.

Each of the elastic securing lace members (341A, 341B, 341*i*, 341*ii*, and 341*iii*) have a first end and a second end, with each of the first ends being fixedly secured to the pull tab 350, as seen in FIG. 17 and FIG. 18. The second end of each of the at least two elastic securing lace members (341A, 341B, 341*i*, 341*ii*, and 341*iii*) respectively pass through the corresponding openings (holes 310Pa, 310Pb, 310Pi, 310Pii, and 310Piii) and may be fixedly secured to the casing 314 in the attachment region shown in FIG. 16. The second end of the elastic securing lace member 341A may be fixedly secured in general proximity to the second end 312 of the flexible casing 314 and in proximity to the proximal end 314 at point 341Ma, such that a theoretical line 341X drawn between that attachment point and the hole 310Pa may be substantially parallel to the proximal end 314 (see FIG. 17). The second end of the elastic securing lace member 341B may similarly be fixedly secured in proximity to the second end of the flexible casing 314 and in proximity to the distal end 313. Where utilized, the second ends of the elastic securing lace members 341*i*, 341*ii*, and 341*iii* are similarly fixedly secured to the flexible casing 314, being equally spaced between the attachment points for the elastic securing lace members 341A and 341B. Note that in one embodiment of the ambidextrous wrist brace 300, the extent of the flexible casing 314 may be as dimensioned in FIG. 16, and preferably uses the five elastic securing lace members (341A, 341B, 341*i*, 341*ii*, and 341*iii*).

The pull tab 350 may generally be formed of the same flexible material as the casing 314; however, while the casing may be formed with a portion of its exterior having either a hook or loop type material secured thereon, one side (or both sides) of the pull tab may be formed with the other of those two materials (e.g., the hook-type material where the loop-type material is used on the outmost layer of the casing), permitting releasable attachment of the pull tab to the casing.

Figure 20:
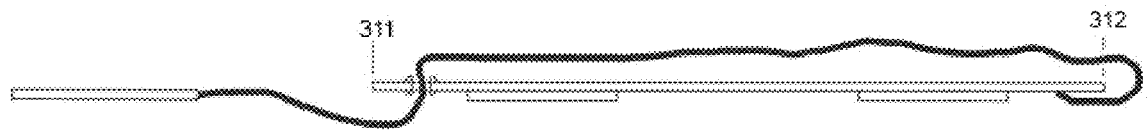
FIG. 20 is a top view of the flexible casing, elastic securing members, pull tab, and flaps, as shown in the flattened configuration of FIG. 19.
Figure 19:
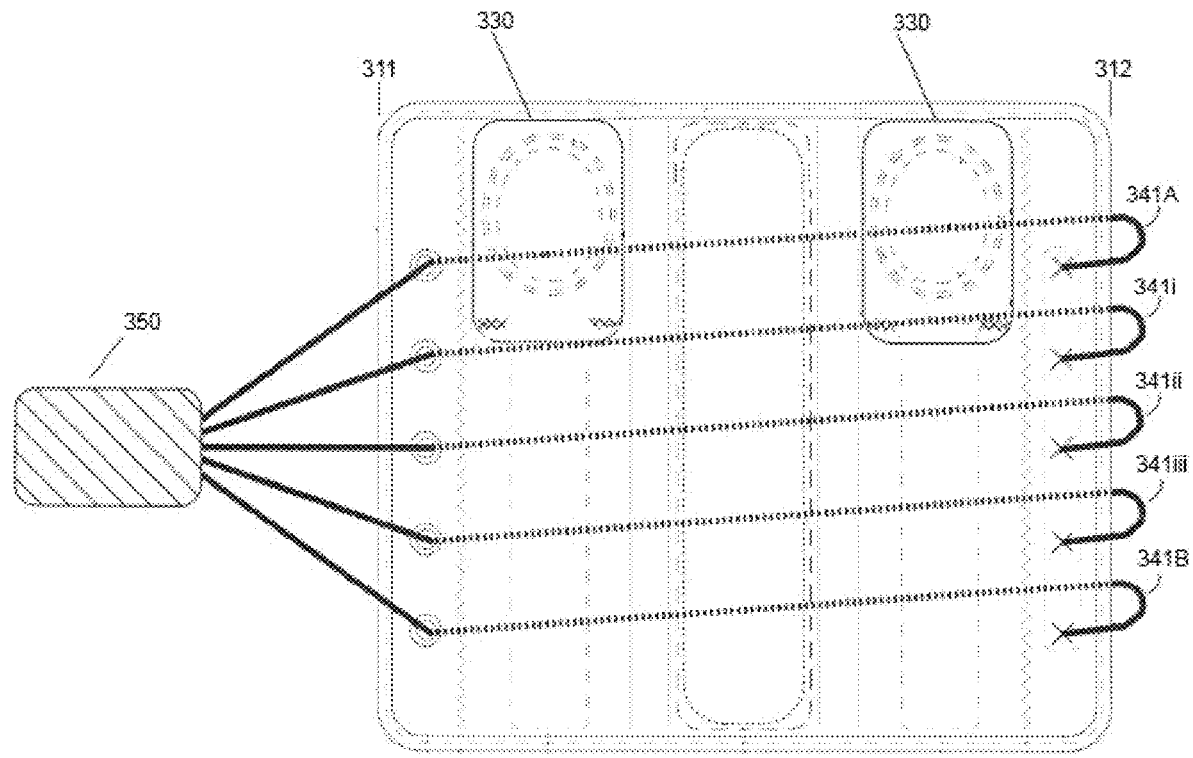
FIG. 19. is the rear view of FIG. 18, but is shown with a pair of flaps releasably secured to the flexible casing, to respectively overlie each of the two thumb sockets.
Figure 21:
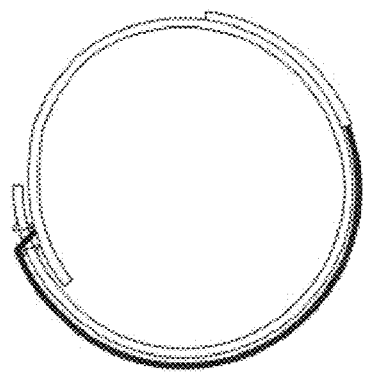
FIG. 21 is the top view of FIG. 20, but shown after the pull tab has been pulled to draw one end of the flexible casing to overlap a second end of the casing in a rounded configuration, and with the pull tab releasably secured to the flexible casing using hook and loop fastening materials.
Figure 21A:
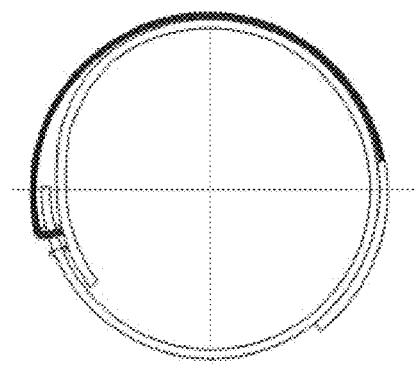
FIG. 21A is the top view of FIG. 21, but shown with the pull tab having been pulled in the opposite direction before being releasably secured to the flexible casing using hook and loop fastening materials.
Figure 22:
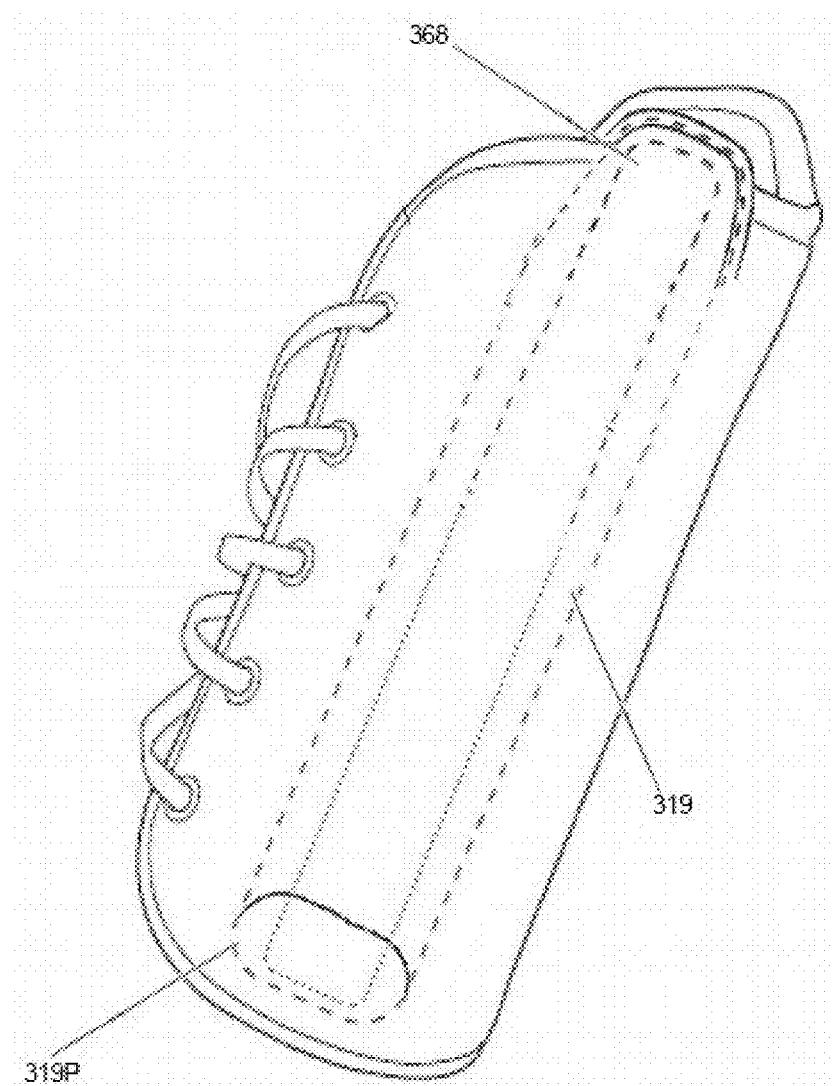
FIG. 22 is a front view of the rounded configuration of the flexible casing, elastic securing members, pull tab, and flaps, as shown in FIG. 21, and which shows an opening at the bottom of the pocket through which a stay will be inserted.

The pull tab 350 may be pulled relative to the casing 314 to change the flat configuration of the casing 314 shown in FIG. 19 and FIG. 20, into a generally circular configuration, whereby the elastic securing lace members (e.g., 341A, 341B, 341*i*, 341*ii*, and 341*iii*) pull the second end 312 of the casing into proximity to the first end 311. The pull tab 350 and elastic securing lace members (e.g., 341A, 341B, 341*i*, 341*ii*, and 341*iii*) may be pulled only enough so that the second end 312 approaches but does not quite reach the first end 311, remaining spaced apart therefrom. Alternatively, the pull tab 350 and elastic securing lace members may be pulled enough so that the second end 312 is aligned with the first end 311, or is positioned beyond the first end 311 for the casing to overlap upon itself, as shown in FIG. 21 and FIG. 21A. The pull tab 350 may be pulled in either a first direction, as illustrated in FIG. 21, or in a second direction, as illustrated in FIG. 21A.

As shown in FIG. 17, the first and second thumb sockets 315/316 permit ambidextrous use of the brace 300, i.e., on either the person's left or right wrist, and the stay 371/372 may be inserted through the appropriate opening 318P or 319P of the pocket 318 or 319 before or after the wearer has applied the casing 314 to his/her left or right wrist. Stay 371/372, when inserted into pocket 318 or 319 supports the inner thumb position and the outer wrist and is completely encased in pockets 318/319 that terminate above the brace at position 367/368, thus extending the support for the thumb or the outer wrist.

A wrist brace 400, which is constructed substantially similar to the herein described wrist brace 300, is shown in FIG. 28 to FIG. 46, and the differences of which are primarily described hereinafter. The wrist brace 400 may include a flexible casing 410 (FIG. 29) that may be substantially similar to the casing 110/310 (i.e., having a center axis 410X, ends 411/412/413/414, and a first thumb socket 415 and a second thumb socket 416), with a plurality of component parts secured thereto, as discussed hereinafter, as well as the plurality of elastic securing laces and a pull tab, which laces and tab are arranged and secured as described hereinabove.

Figure 28:
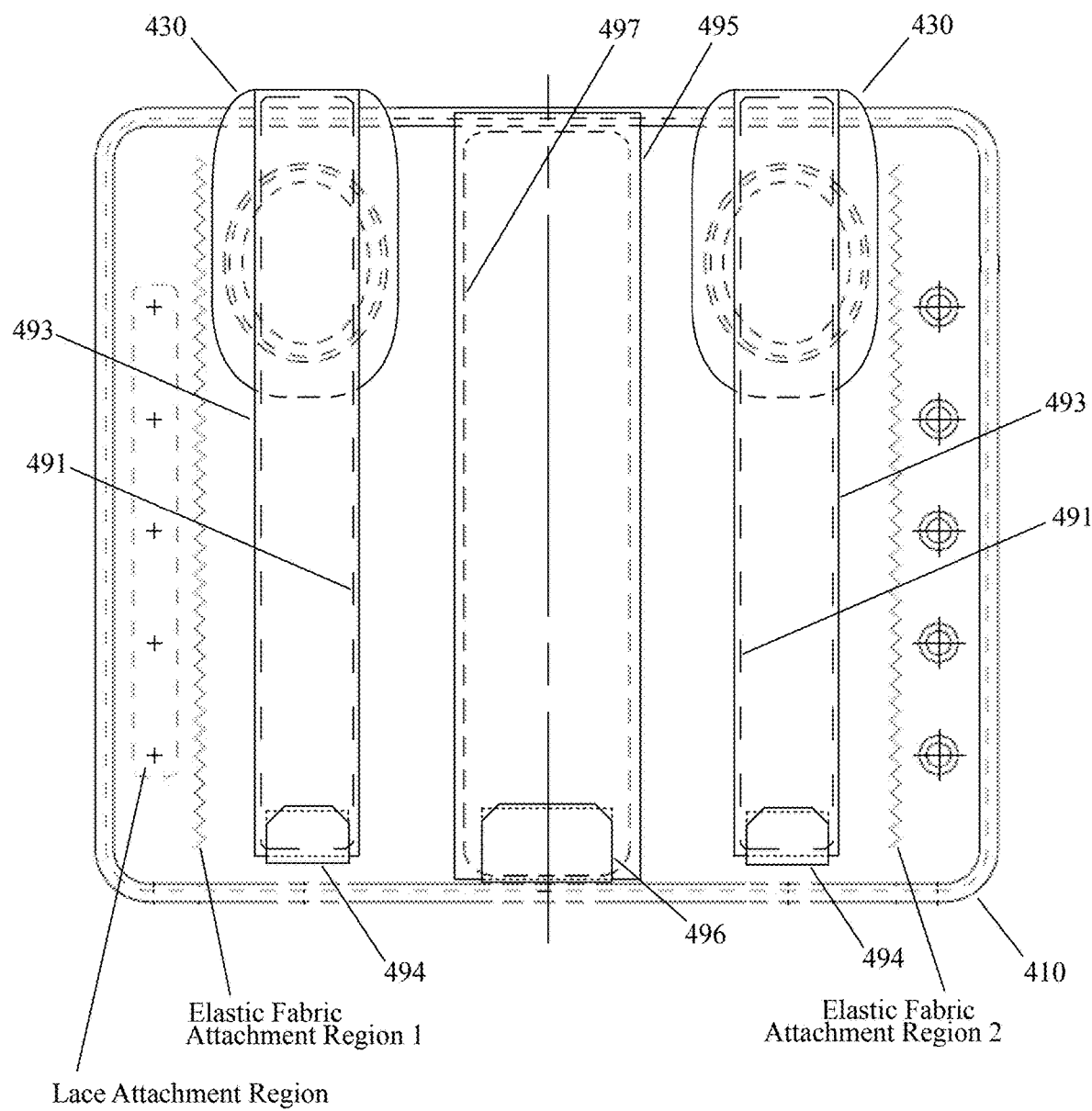
FIG. 28 is a front view of the flexible casing and other components of another wrist brace embodiment, shown assembled together and in a flattened configuration.
Figure 40:
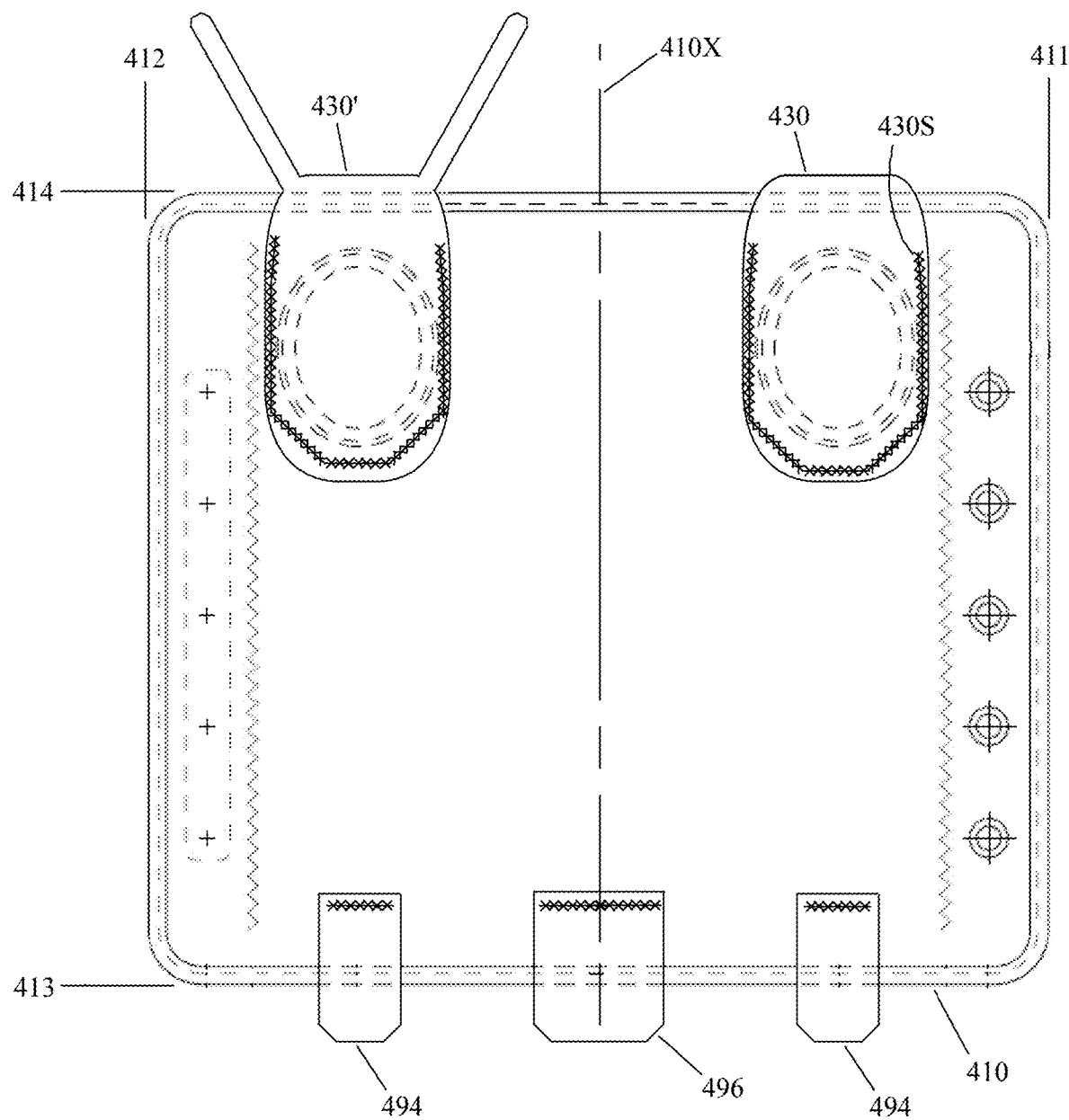
FIG. 40 is the front view of the flexible casing seen in FIG. 28, but shown with a thumb support member of FIG. 30 attached over each thumb socket, and with thumb stay pocket covers of FIG. 32 and a dorsal wrist stay pocket cover of FIG. 28 attached to the casing.

As seen in FIG. 28, the casing 410 may have other components secured thereto, which may include: a pair of thumb support members 430, shown in detail in FIG. 30; a thumb stay pocket member 493, shown in detail in FIG. 31; a thumb stay pocket cover 494, shown in detail in FIG. 32; a dorsal wrist stay pocket member 495, shown in detail in FIG. 35; and a dorsal wrist stay pocket cover 496, shown in detail in FIG. 36, which may form a first elongated pocket formed parallel to the center axis to extend from the proximal end of the casing and terminate in proximity to the distal end of the casing to overlie and extend beyond the first thumb socket, with an opening into the first elongated pocket; and a second elongated pocket formed parallel to the center axis to extend from the proximal end of the casing and terminate in proximity to the distal end of the casing to overlie and extend beyond the second thumb socket, with an opening into the second elongated pocket. A pair of the thumb support members 430 may be fixedly secured to the casing 410 (see FIG. 40) to overlay the thumb sockets using stitching 430S, which stitching does not extend all the way to its distal end, to permit the wearer's thumb to be inserted through an opening thus formed between the casing and the thumb support members. (Note that a thumb support members 430' may instead be formed to include a pair of thumb straps, as shown in FIG. 40, each of which may be looped around the thumb and be releasably secured using hoop and loop materials, to support the thumb of the wearer with respect to the thumb stay). The sides of an elastic material with an opening formed therein may be secured to each of the casing and the thumb support member to limit separation such therebetween (not shown). One side of the pair of thumb stay pocket covers 494, and one side of the dorsal wrist stay pocket cover 496 are also shown fixedly secured to the casing 410 in FIG. 40 using stitching (note that the crisscross stitching shown in FIG. 40, e.g., stitching 430S, is omitted in other views for clarity). Also, as seen therein, a first portion of the first elongated pocket is secured to the casing and a second portion of the first elongated pocket is secured to the first thumb support member; and a first portion of the second elongated pocket is secured to the casing and a second portion of the second elongated pocket is secured to the second thumb support member.

Figure 41:
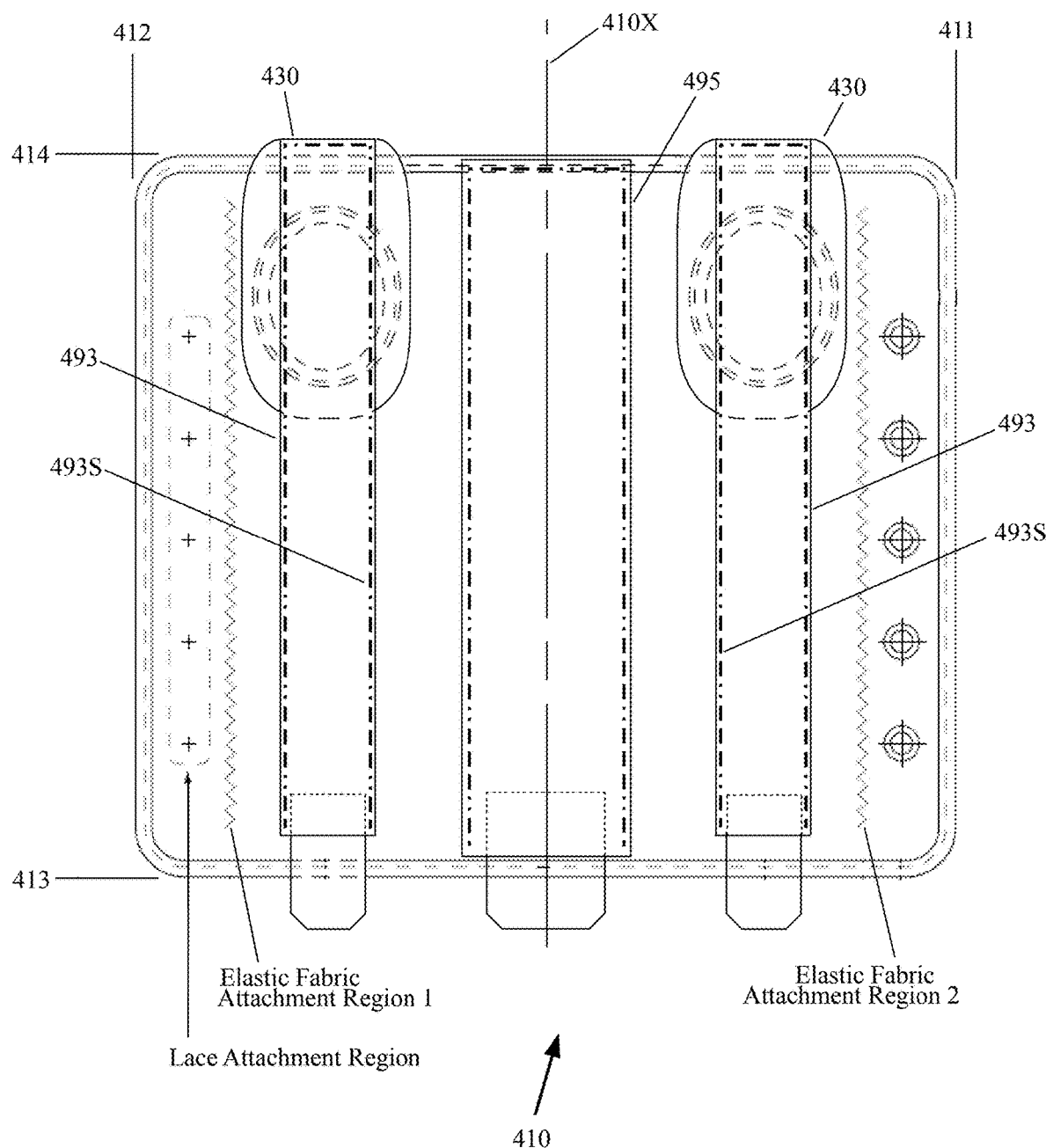
FIG. 41 is the front view of FIG. 40, but shown with a pair of the thumb stay pocket members of FIG. 31 and a dorsal wrist stay pocket member of FIG. 35 fixedly secured thereto to create respective pockets.

FIG. 41 is the front view of FIG. 40, but also shows the pair of the thumb stay pocket members 493 fixedly secured to the casing 410 using stitching 493S, shown with dot-dash lines therein, which thereby form first and second (i.e., left and right-hand) thumb stay pockets. FIG. 41 also shows the dorsal wrist stay pocket member 495 fixedly secured to the casing 410 using stitching to create a dorsal wrist stay pocket.

FIG. 33 and FIG. 34 are front and side views of the thumb stay 491, which is curved to accommodate the outward curvature of the wearer's thumb, when the brace 400 is being worn.

FIG. 37 and FIG. 38 are front and side views of the dorsal wrist stay 497, which may include two bends to accommodate the shape of the dorsal side of the wearer's wrist, knuckles, and hand, when the brace 400 is being worn.

Figure 42:
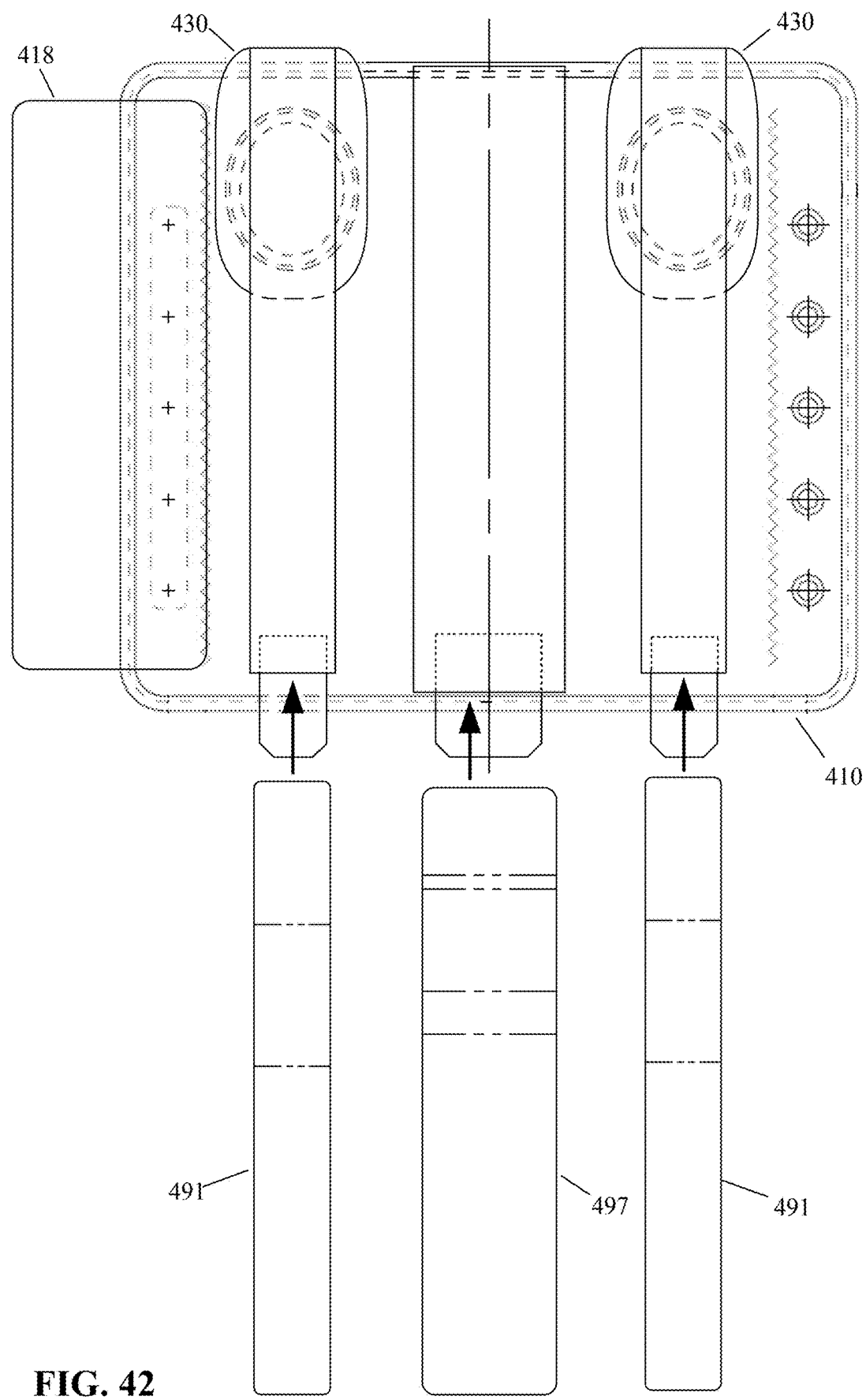
FIG. 42 is the front view of FIG. 41, being shown with a pair of the thumb stays of FIG. 33 and the dorsal wrist stay of FIG. 37 just prior to being inserted into respective pockets.
Figure 43:
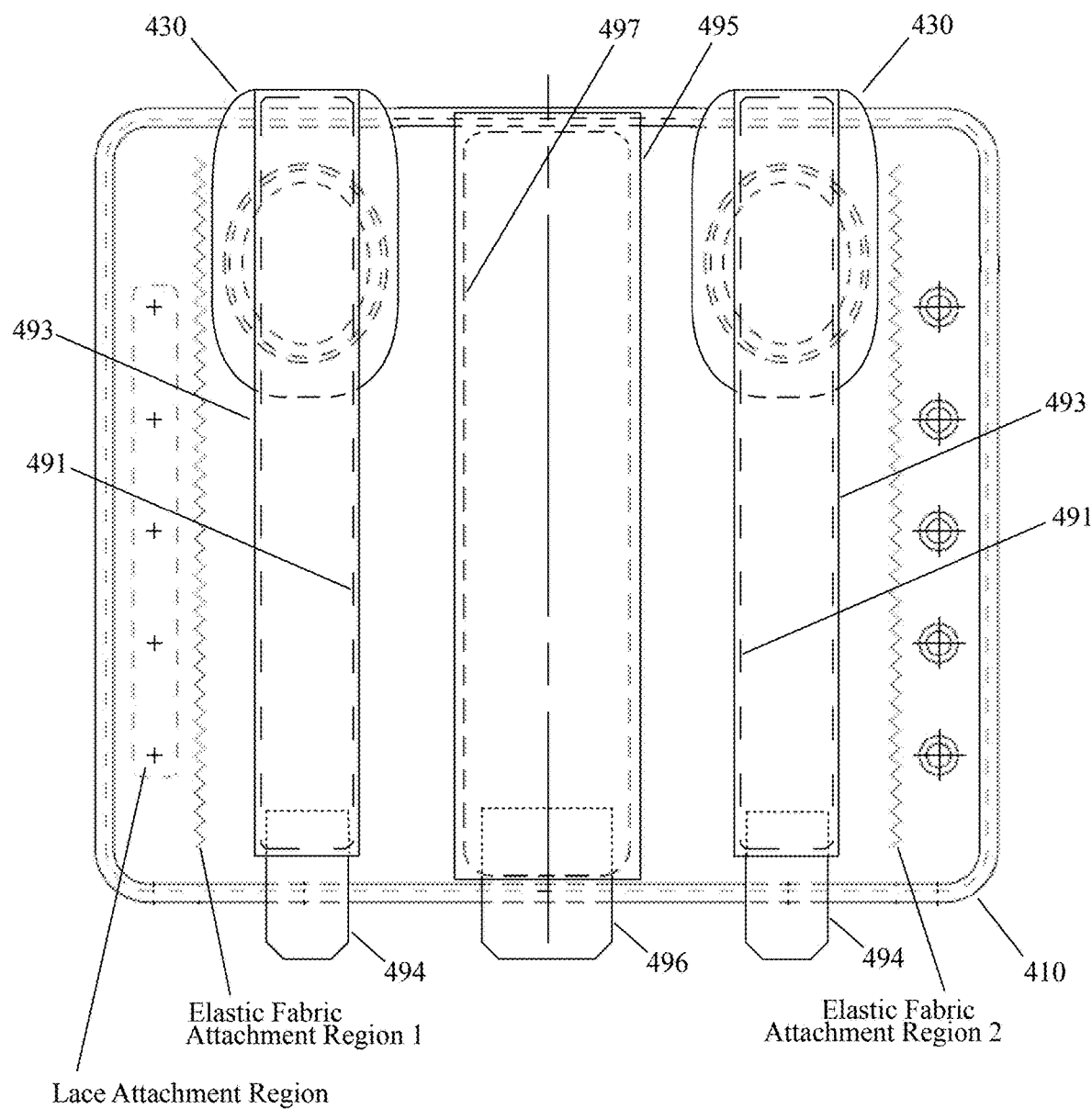
FIG. 43 is the front view of FIG. 42, but shown just after the pair of the thumb stays and the dorsal wrist stay have been inserted into the respective pockets.
Figure 44:
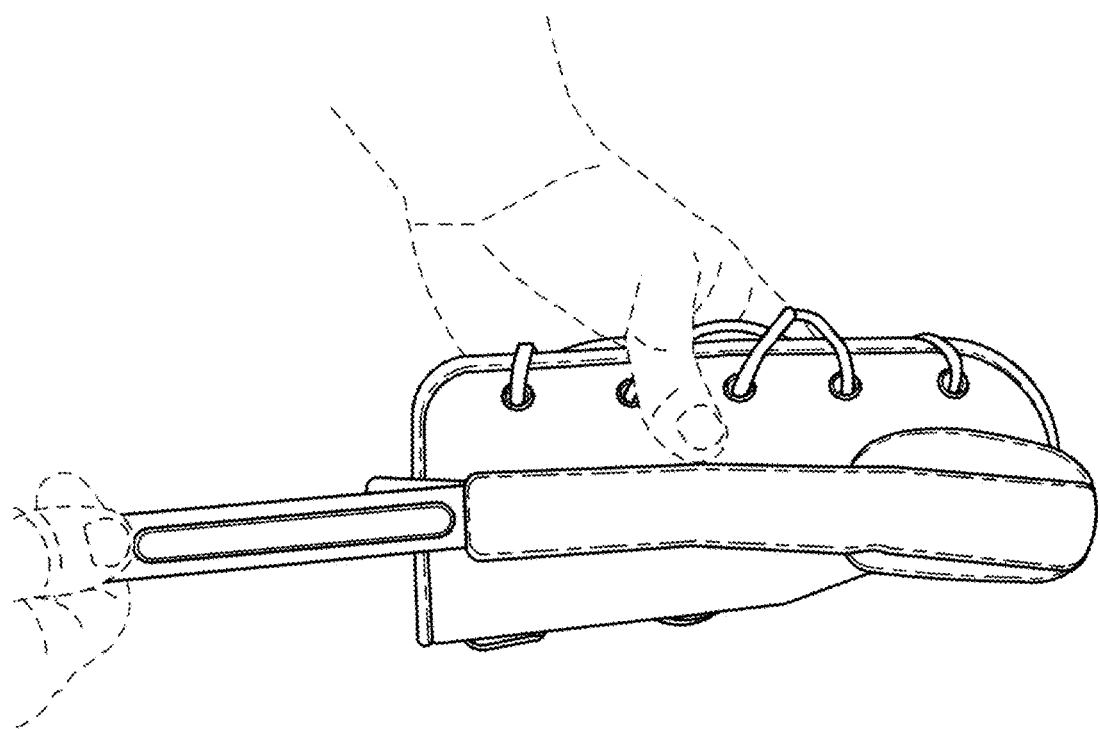
FIG. 44 is a photographic image of a front view of another embodiment of the wrist brace disclosed herein, showing a stay being inserted into one of two pockets on the side of brace.
Figure 44A:
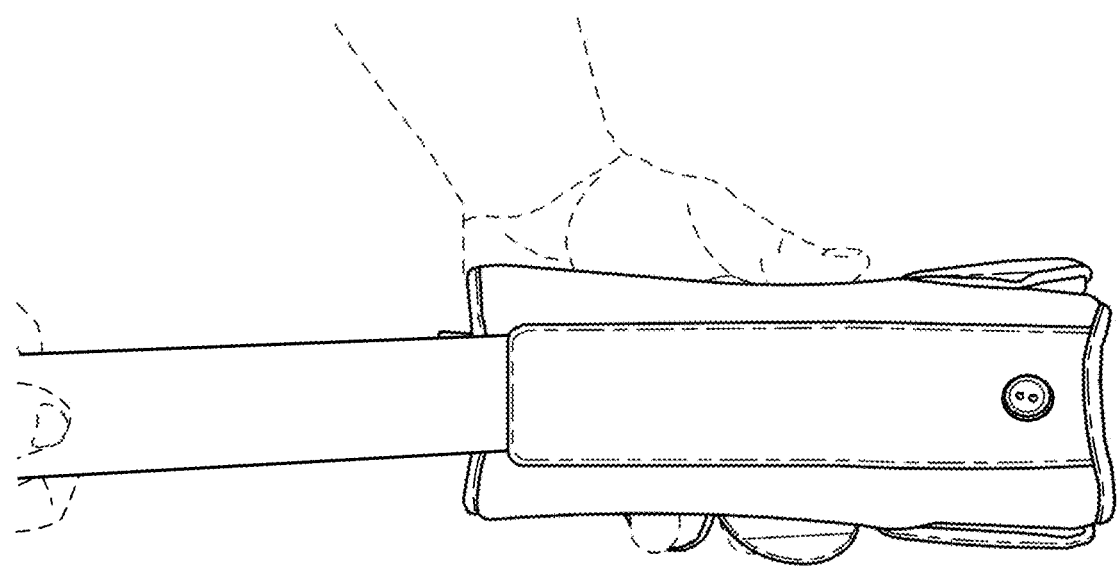
FIG. 44A is a photographic image of the brace of FIG. 28 showing stay a stay being inserted into a central pocket.
Figure 45:
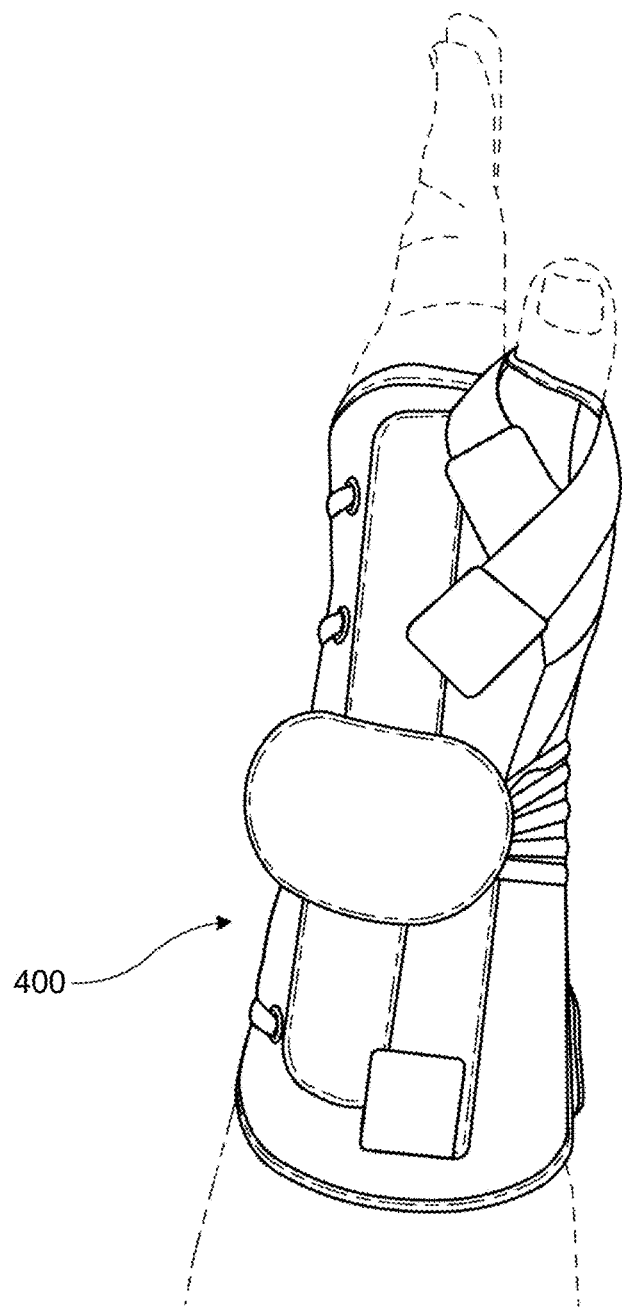
FIG. 45 is a photographic image of the side view of the wrist brace of FIG. 28, but is shown after being secured onto the left hand of a wearer.
Figure 46:
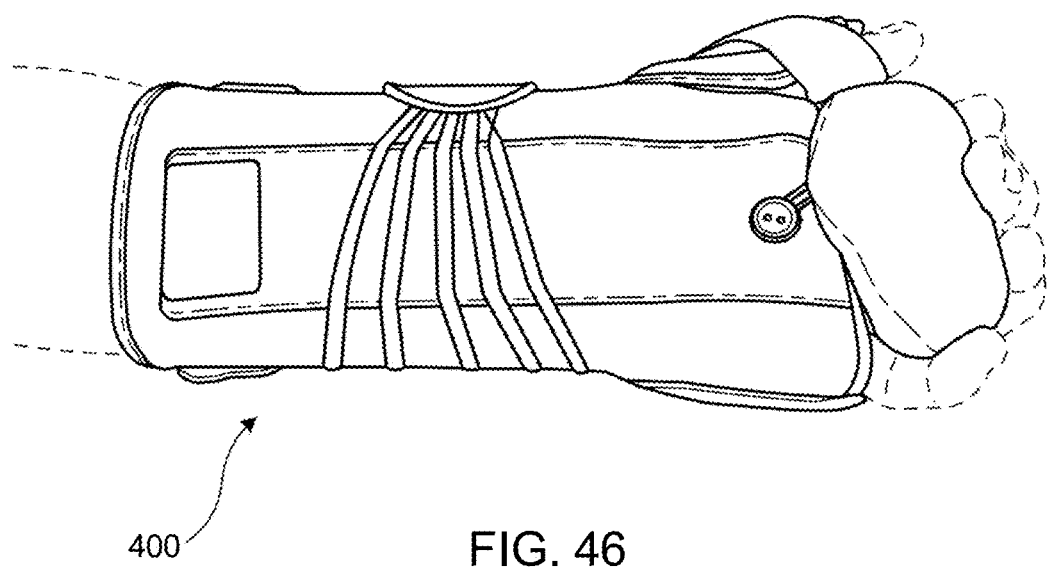
FIG. 46 is a photographic image of the palm view of the wrist brace secured of FIG. 29, shown with a thumb support and medicine ball attached.

FIG. 42 is the front view of FIG. 41, and shows a pair of the thumb stays 491 and the dorsal wrist stay 497 just prior to being inserted into the respective pockets, and FIG. 43 is the same view, but shown just after the pair of the thumb stays and the dorsal wrist stay have been inserted into the respective pockets, and which stays may extend through an entire extent of those respective pockets. FIG. 28 is the front view of FIG. 43, but is shown after the thumb stay pocket covers 494 and the dorsal wrist stay pocket cover 496 have been folded over and releasably coupled, using hook and loop materials, to the thumb stay pocket members 493 and the dorsal wrist stay pocket member 495, respectively.

Figure 29:
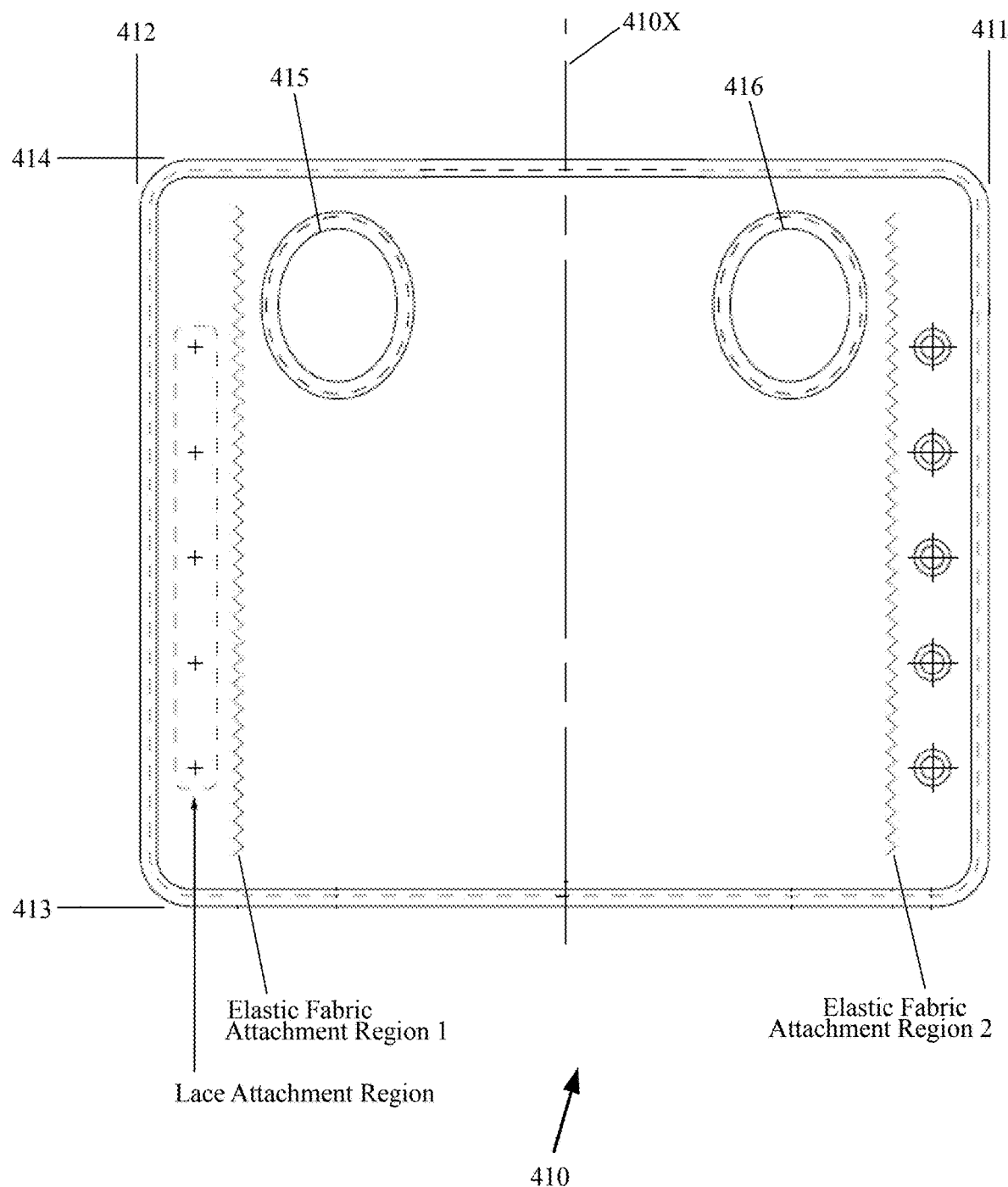
FIG. 29 is a front view of the flexible casing of FIG. 28, shown by itself.

FIG. 39 is a front view of an elastic fabric connector member 418 that may have each of its long sides fixedly secured to the first and second elastic fabric attachment regions shown in FIG. 29, respectively (see FIG. 42), which may form a generally tubular arrangement (see FIG. 6) prior to using the elastic members to draw the ends of the casing together.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A wrist brace configured for alternate use on each of a right hand and a left hand of a wearer, said wrist brace comprising:
 a casing; said casing formed of a flexible material having a quadrilateral shape in a flattened condition, with first and second ends, and distal and proximal ends being symmetric about a center axis, said casing comprising:
  a first thumb socket usable for the right hand and a second thumb socket usable for the left hand, each formed in proximity to said proximal end of said casing, and each positioned symmetrically with respect to the center axis;
 wherein each of said first thumb socket and said second thumb socket comprises an opening with a continuous periphery configured to completely surround the thumb of the wearer when inserted therethrough;
 wherein said opening of each of said first thumb socket and second thumb socket are formed as an oval-shaped opening, with an axial direction of each said oval-shaped opening being oriented parallel to the center axis of said casing;
 a first elongated thumb support member and a second elongated thumb support member, a portion of each of said first elongated thumb support member and said second elongated thumb support member being fixedly secured to said casing to respectively overlay said first thumb socket and said second thumb socket, to permit the wearer's thumb to be inserted through either an opening being formed between said first elongated thumb support member and said casing or an opening formed between said second elongated thumb support member and said casing;
 a first elongated pocket formed parallel to the center axis to extend from said proximal end of said casing and terminate in proximity to said distal end of said casing to overlie and extend beyond said first thumb socket, with an opening into said first elongated pocket;
 a second elongated pocket formed parallel to the center axis to extend from said proximal end of said casing and terminate in proximity to said distal end of said casing to overlie and extend beyond said second thumb socket, with an opening into said second elongated pocket;
 a third elongated pocket substantially centered with respect to the center axis and extending between said proximal end of said casing and said distal end of said casing; and
 at least two holes, each formed in proximity to said first end of said casing;
 a pull tab;
 at least two elastic securing members; each of said at least two elastic securing members positioned to pass through a respective one of said at least two holes; each of said at least two elastic securing members having a respective first end fixedly secured to said pull tab, and a respective second end fixedly secured proximate to said second end of said casing;

a center stay positioned within, and configured to extend throughout, said third elongated pocket;

a thumb stay, said thumb stay configured to be received within either of said first elongated pocket and said second elongated pocket for respective use on the wearer's right hand and left hand, and being further configured to extend through an entire extent of either of said first elongated pocket and said second elongated pocket, to thereby have a portion of said thumb stay extend across a corresponding one of said first thumb socket and second thumb socket;

a strap, said strap configured to loop around a thumb of the wearer, to support the thumb of the wearer against said portion of said thumb stay;

wherein said axial direction of said oval-shaped opening of said first thumb socket is centered and aligned with an axial direction of said first elongated pocket;

wherein an axial direction of said first elongated thumb support member is centered and aligned with said axial direction of said first elongated pocket;

wherein said axial direction of said oval-shaped opening of said second thumb socket is centered and aligned with an axial direction of said second elongated pocket;

wherein an axial direction of said second elongated thumb support member is centered and aligned with said axial direction of said second elongated pocket; and wherein said first elongated pocket, said second elongated pocket, and said third elongated pocket are oriented parallel to each other, and wherein said thumb stay and said center stay are thereby oriented parallel to each other when said thumb stay is received in either of said first elongated pocket or said second elongated pocket and said center stay is received in said third elongated pocket.

2. The wrist brace according to claim 1,
wherein each of said first and second thumb sockets are reinforced with a material stitched thereto.

3. The wrist brace according to claim 2,
wherein said strap comprises a length configured to loop only once around the wearer's thumb to support the wearer's thumb.

4. The wrist brace according to claim 2,
wherein said strap comprises a length configured to loop twice around the wearer's thumb to immobilize the wearer's thumb.

5. The wrist brace according to claim 1 further comprising: a respective grommet secured to said casing at each of said at least two holes.

6. The wrist brace according to claim 1, wherein when said at least two holes comprises five holes, said five holes being equally spaced apart; and wherein said at least two elastic securing members comprises five securing members.

7. The wrist brace according to claim 1,
wherein said opening into said first elongated pocket is formed proximate to said distal end; and
wherein said opening into said second elongated pocket is formed proximate to said distal end.

8. The wrist brace according to claim 1,
wherein said thumb stay is curved to accommodate outward curvature of the wearer's thumb, when said wrist brace is being worn.

9. The wrist brace according to claim 8,
wherein said center stay comprises: two bends being configured to accommodate a shape of the dorsal side of the wearer's wrist, knuckles, and hand, when said wrist brace is being worn.

10. The wrist brace according to claim 1,
wherein a first portion of said first elongated pocket is secured to said casing and a second portion of said first elongated pocket is secured to said first elongated thumb support member; and
wherein a first portion of said second elongated pocket is secured to said casing and a second portion of said second elongated pocket is secured to said second elongated thumb support member.

\* \* \* \* \*